United States Patent [19]

Bjornsson et al.

[11] Patent Number: 4,734,282

[45] Date of Patent: Mar. 29, 1988

[54] RODENTICIDAL COMPOSITIONS CONTAINING 1,4-NAPHTHOQUINONE DERIVATIVES

[75] Inventors: Thorir D. Bjornsson; David M. Cocchetto, both of Durham, N.C.

[73] Assignee: Duke University, Durham, N.C.

[21] Appl. No.: 854,912

[22] Filed: Apr. 23, 1986

[51] Int. Cl.[4] .................... A01N 25/08; A01N 31/06; A01N 31/08

[52] U.S. Cl. .................... 424/410; 514/681; 514/682

[58] Field of Search .................... 514/681, 457, 682; 424/410

[56] References Cited

U.S. PATENT DOCUMENTS

| | | | |
|---|---|---|---|
| 2,396,665 | 3/1946 | Ladd | 514/682 |
| 3,223,231 | 12/1965 | Connolly | 514/681 |
| 4,021,568 | 5/1977 | Suttie | 514/457 |
| 4,310,536 | 1/1982 | Boschetti et al. | 514/681 |
| 4,581,378 | 4/1986 | Zazar et al. | 514/681 |

FOREIGN PATENT DOCUMENTS

| | | | |
|---|---|---|---|
| 486358 | 9/1952 | Canada | 514/682 |
| 2160745 | 7/1973 | France | 514/681 |
| 39-11250 | 6/1964 | Japan | 514/682 |

OTHER PUBLICATIONS

Chem. Abst: 81:115569(g), (1974)–Soxera et al.

Journal of the American Pharmaceutical Association, vol. XLII, No. 6, pp. 379–382, "The Toxicity of 3-(Acetonylbenzyl)-4-Hydroxycoumarin (Warfarin) to Laboratory Animals", by Ernest C. Hagan and Jack L. Radomski.

Journal of American Medical Association, 1943, vol. 65, pp. 1209–1211, "Water-Soluble Derivatives of Menadione", by Amel R. Menotti.

Tetrahedron Letters, 1979, No. 33, pp. 3099–3100, "Oxidation of Aromatic Substrates with Hydrogen Peroxide and Hydrochloric Acid", by P. Thirumalai Perumal and M. Vivekananda Bhatt.

Bull. Sté. Chim. Biol., 1948, 30, No. 11–12, pp. 863–872, "Vitamines K et Anti-Vitamines K en Microbiologie", by Guérillot-Vinet.

Science, 1973, vol. 180, pp. 741–743, "Anticoagulant-Resistant Rats: Possible Control by the Use of the Chloro Analog of Vitamin $K_1$", by J. W. Suttie.

*Primary Examiner*—Douglas W. Robinson
*Attorney, Agent, or Firm*—Oblon, Fisher, Spivak, McClelland & Maier

[57] ABSTRACT

A food composition for poisoning a rodent, which comprises a rodent foodstuff which contains as an active rodenticidal agent, a lethal or sub-lethal quantity of a compound having the formula:

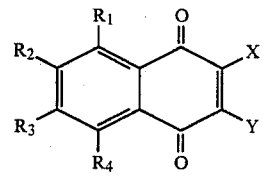

wherein X is Cl, Br, F, or I; Y is H, Cl, Br, F, I, $-SO_3H$, $SO_3Na$, or $-SO_3K$; and $R_1$-$R_4$ are each independently H, Cl, Br, F, I, $C_1$-$C_6$ alkyl, $C_1$-$C_6$ alkoxyl, or $C_1$-$C_6$ alkoxyalkyl or a hydroquinone analogue of the compound, and a method for controlling rodents using said composition.

18 Claims, 19 Drawing Figures

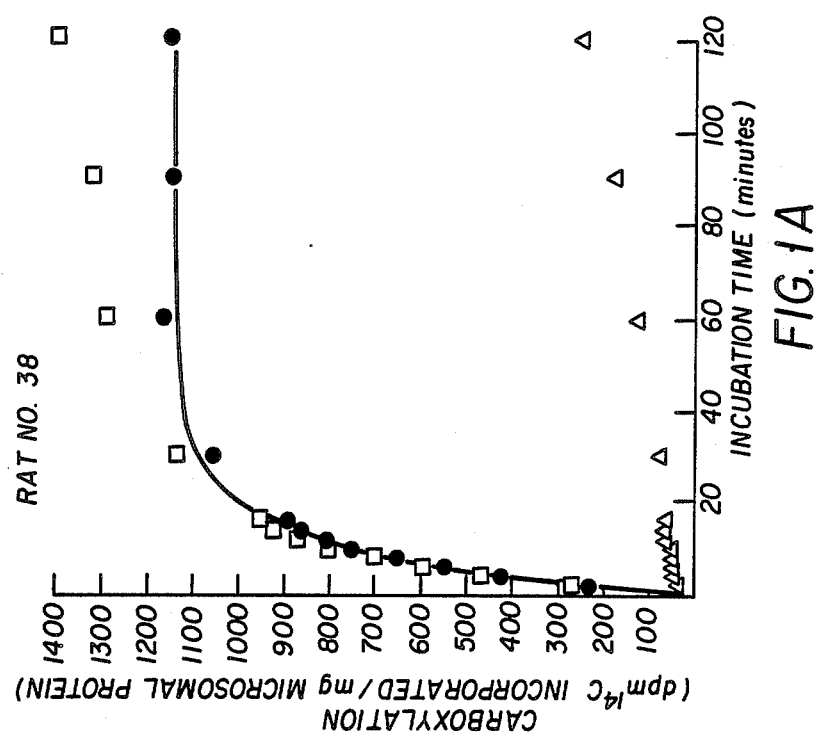

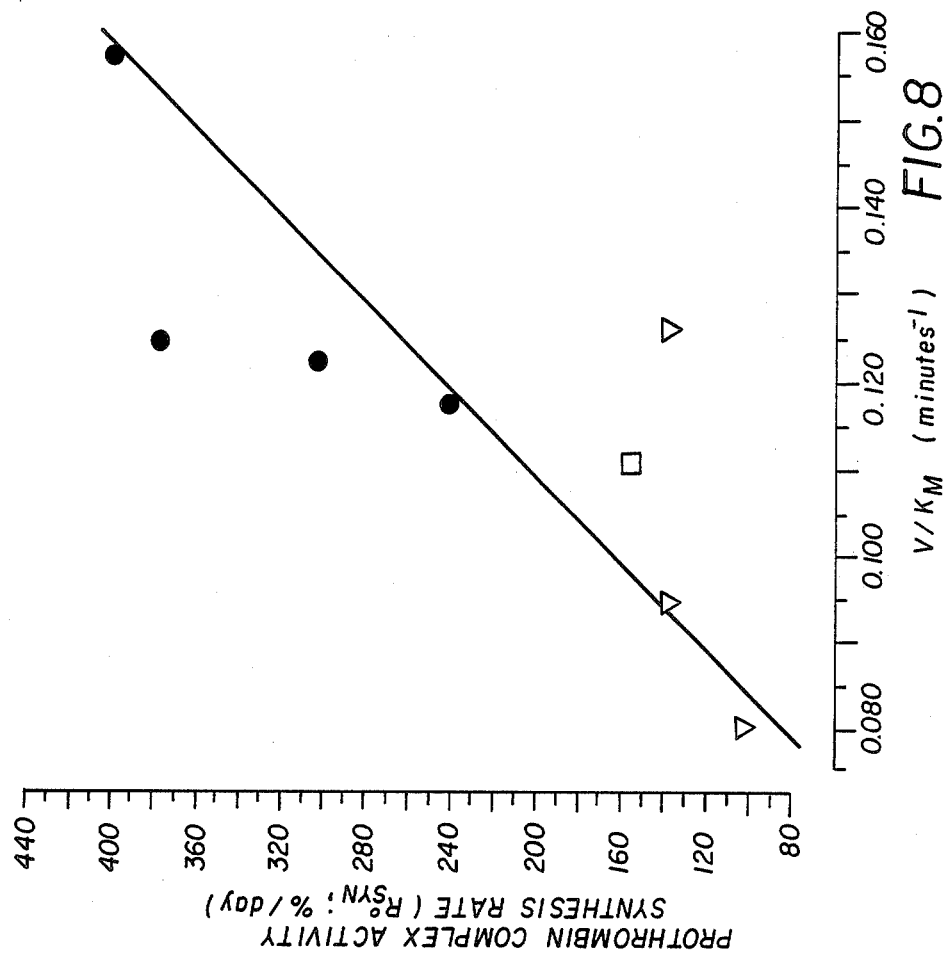

RODENTICIDAL COMPOSITIONS CONTAINING 1,4-NAPHTHOQUINONE DERIVATIVES

BACKGROUND OF THE INVENTION

1. Field of the Invention

The present invention is related to rodenticidal compositions containing 2-chloro-1,4-naphthoquinone and closely related derivatives thereof. The invention is also related to methods of killing rodents using the compounds disclosed herein.

2. Description of the Prior Art

The control of rodent populations is a problem in many areas of the world. In addition to their attacks on man's food, rodents also harbor vectors of many diseases of man and domesticated animals. Rodent-derived diseases include Bubonic plague, Weils disease, endemic typhus, scrub typhus, Rocky Mountain spotted fever, and various salmonella-derived diseases which are contracted by handling objects contaminated by rodent urine or feces.

A number of chronic poisons had been developed for killing rodent pests. Chronic poisons are those which generally require several feedings to produce a lethal effect. One type of chronic poison is the group having anticoagulant activity. There are a wide range of chronic anticoagulant rodenticides, and these each share a common mode of action involving antagonism of Vitamin K action.

Vitamin $K_1$ is an important blood coagulation co-factor. Vitamin $K_1$ is essential for coagulation because of its role in the synthesis of four clotting proteins, all of which are capable of binding calcium and are essential for the cascade mechanism leading to the formation of thrombin and thus, blood coagulation. Anticoagulants interfere with the metabolism of Vitamin $K_1$, resulting in decreased Vitamin K-dependent carboxylation of the clotting factors. Without vitamin $K_1$ to act as a co-factor, thrombin formation is inhibited, the blood loses its ability to coagulate, and death can result from spontaneous hemorrhaging.

A number of compounds which are structurally related to vitamin K can function as anti-coagulants, among which those with coumarin ring systems are notable. Two anticoagulants of note are dicumarol (a clinically effective anticoagulant) and warfarin (used both clinically and as a rodenticide).

The use of the natural anticoagulant dicoumarol as a rodenticide was first described in 1948 by O'Connors (Research 1, 334 (1948)). Other 4-hydroxy-coumarins have been described, some of which are more effective than warfarin itself. See Kirk Othmer's Encyclopedia of Chemical Technology, Vol. 18, 302–320, 1981, which is hereby incorporated by reference.

Another type of anticoagulant rodenticide is based on indanedione. Some of these compounds are as effective as warfarin or the other 4-hydroxy-coumarins although few, if any, of these compounds are used commercially.

Lowenthal, in a series of reports, has shown that a competitive vitamin K antagonist which is neither a hydroxy coumarin or an indanedione is also an active anticoagulant. (See J. Pharmacol. Exp. Ther. 157 (3), 672–80, 1967; Experientia 16, 428–9, 1960; and Canadian Journal Chemistry, 48, 3957–58, 1970.) The compounds studied in these references are vitamin $K_1$ analogues, primarily 2-chloro-3-phytyl-1,4-naphthoquinone. In this analogue, a chlorine atom is substituted for the methyl group of Vitamin $K_1$. Lowenthal's work was continued by Suttie and co-workers and reported in Science, 180, 741–43, 1973 and patented by Suttie in U.S. Pat. No. 4,021,568. Suttie disclosed a rodenticide based on the chloro analogue of vitamin $K_1$ and showed that it was effective against strains of wild rats that were resistant to the anticoagulant action of coumarins and derivatives of indanedione. Suttie further showed that the compound could be used either alone or in combination with warfarin. However, this compound proved to be difficult to synthesize and chemically unstable. Accordingly, although it exhibits a relatively high degree of toxicity to warfarin-resistant rats, it has not found overwhelming usage because of these drawbacks. None of the compounds disclosed herein contain the phytyl side-chain of the compounds investigated by Lowenthal and Suttie.

2-chloro-1,4-naphthoquinone, one of the compounds of the present invention, is a known compound, although not for the purpose of a rodenticide. For example, Perumal showed a relatively simple synthesis of this compound in Tetrahedron Letters 33, 3099–3100, 1978. However, absolutely no utility was disclosed for the compound in this reference.

Guerillot-Vinet presented a study of the activity of anti-Vitamin K agents against bacteria. In passing, the reference indicates that 2-chloro-1,4-naphthoquinone has hemorrhagic activity. However, no further information on this compound is given in this reference, and it is unclear from the reference whether this compound would be suitable as a rodenticide.

There are several factors to be considered in deciding whether a particular compound which exhibits hemorrhagic activity can be used as a rodenticide. For example, such factors as stability of the compound in a food or bait environment, ease of synthesizing the compound, activity in vivo of the compound, the attractiveness of the compound to the animal to be poisoned, and the degree of selective toxicity of the compound for the rodent compared with both man and non-rodent wildlife animals. Guerillot-Vinet says nothing about the ability of this compound to be used as a rodenticide, and based on this reference, it is not predictable whether the compound could be so used. The present inventors quite surprisingly discovered that 2-chloro-1,4-naphthoquinone (and closely related derivatives) may be used in vivo as rodenticides and that both in vitro and in vivo activities of this compound are distinctly superior to warfarin and the chloro-$K_1$ compound disclosed by Lowenthal and Suttie.

Using an in vitro rat hepatic vitamin K-dependent carboxylation system (described herein in the experimental examples), 2-chloro-1,4-naphthoquinone was found to be 45 times more potent than warfarin. An in vivo test of toxicity of 2-chloro-1,4-naphthoquinone in the rat, conducted by administering a single intravenous bolus dose showed that the acute lethal intravenous dose of this compound lies between 1 ng/kg and 1000 ng/kg. Thus, this compound is approximately $2 \times 10^5$ to $2 \times 10^8$ times more potent than intravenously administered warfarin, assuming an $LD_{50}$ for warfarin of 0.2 mg/kg (the $LD_{50}$ for warfarin may actually be as high as 10–50 mg/kg in rats, indicating an even larger difference in potency).

In view of the fact that new and more effective agents for the control of rodents are a constant necessity, due primarily to the fact that many strains of rodents have become resistant to known rodenticides, a need continues to exist for such agents. It was in this context that the present invention was achieved.

SUMMARY OF THE INVENTION

Accordingly, it is an object of the present invention to provide a new composition having rodenticidal activity.

It is a further object of this invention to provide a method for controlling rodents, which comprises administering to a target rodent a rodenticidal composition.

These and other objects of the present invention as will hereinafter become more readily apparent, have been accomplished by providing a rodenticidal composition suitable against rodent populations, wherein the essential rodenticidal ingredient is a compound having the following formula:

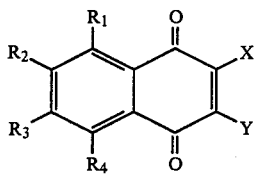

wherein X is Cl, Br, F, or I; Y is H, Cl, Br, F, I, $-SO_3H$, $-SO_3Na$, or $-SO_3K$; and $R_1-R_4$ are each independently H, halogen, $C_{1}$-alkyl, $C_{1-6}$ alkoxy or $C_{1-6}$ alkoxyalkyl.

The invention further encompasses hydroquinone derivatives of the above compounds, having the following formula:

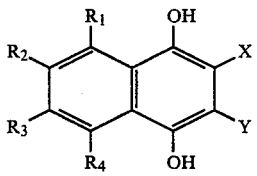

wherein X, Y and $R_1-R_4$ are defined above.

The present invention is also directed to a method of controlling rodent populations which comprises providing to said rodents for consumption, a food or drink composition comprising a lethal or sub-lethal amount of a compound having the formula given above.

BRIEF DESCRIPTION OF THE DRAWINGS

A more complete appreciation of the invention and many of the attendant advantages thereof will be readily obtained as the invention becomes better understood by reference to the following detailed description and examples when considered in connection with the accompanying drawings, wherein:

FIG. 8. Relationship between in vivo rate of synthesis of prothrombin complex activity (R°$_{syn}$) and the in vitro intrinsic formation rate of carboxylated vitamin K-dependent proteins (V/$K_M$). Parameters shown were observed in normal (●), ANIT-pretreated (□), and $CCl_4$-pretreated (∇) rats. The linear least-squares regression line is superimposed (r=0.787 [0.01<p<0.05]; $\tau_b$=0.643).

DESCRIPTION OF THE PREFERRED EMBODIMENTS

Figure 1D:
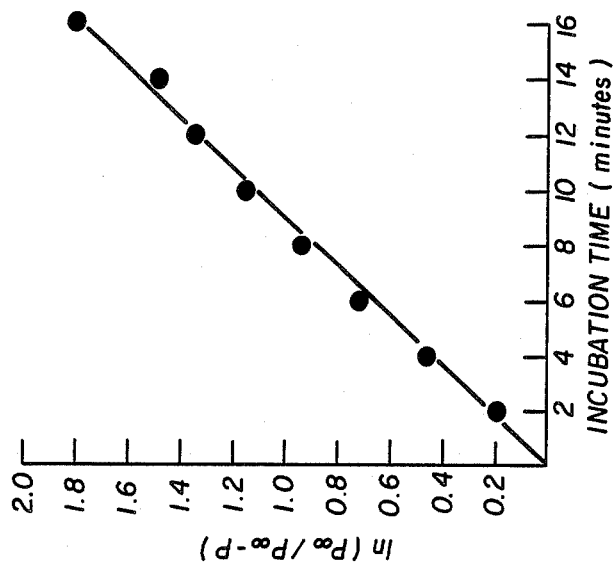
FIG. 1. Time course of vitamin K-dependent carboxylation of endogenous substrate in rat #38 (upper panel) and rat #48 (lower panel). Left side graphs illustrate total carboxylation (□), carboxylation in the absence of vitamin K (Δ), and resulting vitamin K-dependent carboxylation (●). The nonlinear least-squares regression curve is shown for the vitamin K-dependent data. Right side graphs show the corresponding plots according to the product accumulation rate plot (r>0.990 for both lines).

The present invention provides a new use of the compound 2-chloro-1,4-naphthoquinone and closely related derivatives thereof as the active ingredient in a rodenticidal composition. Further, the present invention provides a new method for control of rodents which comprises providing for consumption by the rodents a composition containing at least one of the compounds of the invention.

The present invention is based on the discovery that the compounds disclosed herein are effective rodenticidal agents. They may be administered to rodents by any means known to those skilled in the art. They may be combined with any ingredients which increase the chances that they will be ingested by a rodent. They may further be combined with any ingredient which enhances their poisonous effect, such as other known poisonous materials (see below).

In the present invention, when a solid food is used as a bait to be combined with the rodenticide, it can be any edible product suitable for rodents, such as, for example, cracked corn, corn meal, mixtures of various grains, e.g. mixtures of corn, oats, and wheat, ground meat, and mixtures of meat and grain, etc. From the viewpoint of safety, it is preferred to use a grain base which, while attractive to the rodent, is not as attractive to children and household pets as a bait. The final bait mixtures can be used as such or pelleted or shaped in accordance with standard practices in the art.

The food material may also be a liquid or a semi-solid. The liquid may be any liquid which does not react with the rodenticidal compound and which is suitable for ingestion by a rodent. Liquids such as water, milk, syrup, carbonated flavored liquids, etc. may be employed. The semi-solid may be a fatty, gum-based or gelatinous material, such as animal fat, carbohydrate gums, etc.

By a rodent is meant a vertebrate which is a member of any of the classes of the phylum Chordata. The most significant pest species desired to be controlled are among the order Rodentia, class mammalia. More particularly, the rodents which are desired to be controlled in the present invention are the black or ship rat, *Rattus rattus*, the roof rat, *Rattus alexandrinus*, the house mouse, *Mus musculus*, the gray or brown rat, *Rattus norvegicus*; and the bandicoot rat of Southeast Asia, *Bandicota bengalensis*. Among the species that attack growing crops or destroy pasture are the vole, gopher, the great tree squirrel, and ground squirrel. Certain species of rabbits are also included within this class. Most commonly, the rat or mouse will be the rodent which is desired to be controlled (poisoned).

The amount of a compound of the present invention which is effective against the target rodent, can be easily determined in vivo by simply feeding various amounts of the substance to the rodent, and determining if a poisonous effect (e.g., death or debilitation) is exhibited after a suitable pre-determined period of time. If the rodenticide is contained in a chronicpoison amount, the period of time required will be on the order of several days (i.e., 2-10 days, usually around 3-5 days). If an acute-poison amount is involved, the effects will be exhibited in minutes (i.e., 1-30 minutes), depending on the precise dosage administered.

Generally, if the rodenticide is to be used as a chronic poison, the weight percent of the rodenticidal compound should be in the range of 0.00001 to 0.1 wt. % relative to the solid food or liquid. Preferably, the weight range will fall in the range of 0.0005 to 0.05 to wt. % relative to the solid food or liquid. More preferably, the range will be 0.001 to 0.01 wt. % relative to the solid food or liquid.

The compounds of this invention are defined structurally above. In the formula; $R_1$-$R_4$ may each be an alkyl group having up to six carbon atoms which may be a straight chain, branched or cyclic alkyl group, such as methyl, ethyl, propyl, iso-propyl, butyl, iso-butyl, sec-butyl, hexyl and cyclohexyl. $R_1$-$R_4$ may also be an alkoxy group having up to six carbon atoms, such methoxy, ethoxy, propoxy, iso-propoxy, butoxy, sec-butyl, pentoxy, cyclohexyloxy, etc. $R_1$-$R_4$ may further be an alkoxy alkyl group having up to six carbon atoms, such as $CH_3$—O—$CH_2$—, $CH_3CH_2$—O—$CH_2$—$CH_2$—, $CH_3CH_2CH_2$—O—$CH_2$—, and branched and/or cyclic derivatives. Each of the above groups may also be substituted by up to three halogens, amino, hydroxyl groups and/or keto moieties.

X may be Cl, Br, or F. Y is selected from H, Cl, Br, F, I, —$SO_3H$, —$SO_3Na$, and —$SO_3K$.

These groups may be present so as to adjust the solubility of the final compound. For example, amino groups and hydroxyl groups may be substituted on the side chain to increase aqueous solubility if desired.

In a preferred embodiment at least three of $R_1$-$R_4$ are hydrogen. In a more preferred embodiment each of $R_1$-$R_4$ and Y are hydrogen.

Specific compounds included in this invention are the following: 2-chloro-1,4-naphthoquinone; 2-chloro-1,4-naphthohydroquinone; 2-bromo-1,4-naphthoquinone; 2-bromo-1,4-naphthohydroquinone; 2-fluoro-1,4-naphthoquinone; 2-fluoro-1,4-naphthohydroquinone; 2-iodo-1,4-naphthoquinone; and 2-iodo-1,4-naphthohydroquinone. The most preferred compound of the present invention is 2-chloro-1,4-naphthoquinone.

The compounds according to the present invention may be synthesized by known techniques. Two suitable procedures are described by Bratt and Suschitzky, J. Chem. Soc., 16, Perkins Translation 1, 1689-1693 (1973); and Perumal and Bhatt, Tetrahedron Letters, No. 33, 3099-3100 (1979), which are hereby incorporated by reference. These two references disclose syntheses for the 2-chloro-1,4-naphthoquinone derivative. The other 2-halogeno derivatives may be synthesized analogously, but starting with the appropriate halogenated starting material.

The naphthohydroquinones may be synthesized in a manner analogous to the synthesis of 2-chloro-3-phytyl-1, 4-naphthohydroquinone, as described by Lowenthal, Can. J. Chem. 48, 3957-58, 1970, which is hereby incorporated by reference. The bisulfite addition products (Y=—$SO_3H$, —$SO_3Na$, or —$SO_3K$) may be prepared by the method reported by Menotti, J. Am. Chem. Soc. 65, 1209-11 (1943). Additional products with other nucleophilic reactants are also encompassed by this invention. The invention further encompasses the hydrated compounds, such as the mono, sesqui, di and tri hydrates of the compounds referred to herein.

Any other method which is known in the literature or which is subsequently developed for synthesizing these compounds could also be used.

The food compositions of the present invention may be prepared by dissolving the compounds described above in a solvent and then adding the solvent to a food composition, or simply supplementing the food composition with undissolved compound. Furthermore, other rodenticides may be included with the rodenticides of the present invention.

The other rodenticides may be any of those mentioned herein, or any of those listed in Kirk-Othmer's Encyclopedia of Chemical Technology, Volume 18, 302-320 (1981). When other rodenticides are used in combination with one or more of those of this invention, the total percentage of one or more of the present compounds should be in the range of 0.00001 to 0.1% based on the total weight of the food composition. More preferably, the range should be 0.0005 to 0.05%. The most preferred range is 0.001 to 0.01%.

Other ingredients can also be included with the food composition according to the present invention. For example, various attractive agents such as odorattractive chemicals, sterilants, binders, antioxidants, sweeteners, fillers, and any other inactive ingredient can be included in the food composition according to this invention. Ingredients of this type are well known to those of skill in the art.

The food composition can further comprise a liquid component in any wt. %, as long as the active compound according to this invention is contained therein in a weight percentage as recited hereinabove. The liquid compound can be water, a lower alcohol, milk, other organic solvents, mixtures of organic:aqueous solvents, sweetened beverages, etc.

The method of the present invention involves preparing a food composition as described above, and formulating it in a form such that it is attractive to the target rodent. The size and shape of the particular food composition can be any which is known to those of skill in the art to be attractive and suitable for delivering a rodenticidal material.

The invention now being generally described, the same will be better understood by reference to certain specific experimental examples which are included herein for purposes of illustration only and are not intended to be limiting of the invention or any embodiment thereof, unless specified.

EXPERIMENTAL EXAMPLES

Vitamin $K_1$ (phylloquinone; phytonadione; 2-methyl-3-phytyl-1, 4-naphthoquinone) is a cofactor for post-translational gamma-carboxylation of specific glutamyl residues in the four classical vitamin K-dependent proteins of the hemostatic system (CRC Crit. Rev. Biochem. 8, 191–223; Molecular and Cellular Biochem. 38, 77–121 and 39, 191–207; Drugs and Nutrients. The Interactive Effects, 429–473). Studies by other groups have demonstrated that the rat hepatic microsomal system is useful for studying the vitamin K-dependent carboxylation reactions. Assay methods have used either synthetic peptides (J. Biol. Chem. 251, 5827–5830; FEBS Lett. 75, 226-230) or the endogenous precursors that accumulate in the rat liver during diatary vitamin K deficiency or after warfarin administration (J. Biol. Chem 250, 4744–4748) as substrates for the vitamin K-dependent carboxylase. Despite numerous studies of various properties and requirements for vitamin K-dependent carboxylation in the rat hepatic microsomal system, this system has not been widely utilized as a means of studying the biochemical pharmacology of anticoagulants which exert their effects as vitamin K antagonists. Investigations on warfarin have involved single-time point determinations of percentage inhibition of vitamin K-dependent carboxylation of endogenous substrates in a detergentfree (J. Biol. Chem. 251, 2770–2776) and a detergentsolubilized (Biochemistry 17, 1371–1377) microsomal system. In the solubilized system, warfarin's efficacy is considerably diminished. Available data on comparative anticoagulant potency involve single-time point data on percent inhibition of prothrombin synthesis in a detergent-free microsomal cytosolic system, using two-stage prothrombin time assays, versus various coumarin and indanedione anticoagulants. These vitamin K antagonists are ranked in decreasing order of potency as 3-phenyl-4-hydroxycoumarin > phenindione > dicumarol > coumatetralyl ≃ marcoumar ≃ indanedione > 4-hydroxycoumarin > S(−)warfarin > R(+)warfarin (Biochem. Biophys. Res. Commun. 72, 619–625; Biochem. Pharmacol. 30, 1953–1958). Comparative anticoagulant potency data determined by well characterized studies of in vitro vitamin K-dependent carboxylation are not available for the various coumarin and indanedione compounds.

The first objective of the experiments described below was to develop a reproducible kinetic method for quantitation of in vitro rat hepatic microsomal vitamin K-dependent carboxylation using the endogenous substrates, and subsequently, to determine the percent inhibition versus concentration relationship for selected vitamin K antagonists. The antagonists selected represented different groups of chemicals and they were warfarin (a coumarin), phenindione (an indanedione), 2-chloro-1,4-naphthoquinone and 2-chloro-3-phytyl-1, 4-naphthoquinone (chlorinated analogues of vitamins $K_3$ and $K_1$, respectively), 2,3,5,6-tetrachloropyridin-4-ol (an experimental rodenticide), and 2,6-dichloroindophenol sodium (a potent inhibitor of DT diaphorase). These chemically representative antagonists may serve as useful tools in characterizing selective perturbations of the regulatory mechanisms of vitamin K-dependent carboxylation.

The second objective of the experiments described below was to determine whether there exist relationships between the in vitro kinetic parameters of microsomal vitamin K-dependent carboxylation using the endogenous substrates and the in vivo plasma activity and rate of production of circulating vitamin K-dependent coagulation factors. The existence of such relationships might suggest mechanisms underlying the regulation of synthesis of vitamin K-dependent coagulation proteins.

Materials:

OCS and NCS were from Amersham Corporation (Arlington Heights, IL). $^{14}C$-sodium bicarbonate (specific activity=41–54 mCi/mmol) was from New England Nuclear (Boston, Mass.) or Amersham Corporation. Warfarin, phenindione, 2,6-dichloroindophenol sodium (2,6-DIP), α-naphthylisothiocyanate (ANIT), NADH, phosphocreatine, ATP, creatine phosphokinase, and Tween 80 were from Sigma Chemical Co. (St. Louis, Mo.). Dithiothreitol was from Bachem (Torrance, Calif.). Phenobarbital sodium U.S.P. was obtained from Mallinckrodt, Inc. (Paris, Ky.). AquaMEPHYTON (MSD, West Point, Pa.) was used as a source of vitamin $K_1$. 2,3,5,6-Tetrachloropyridin-4-ol (TCP) and 2-chloro-1,4-naphthoquinone (chloro-$K_3$) were synthesized by published procedures (J. Chem. Soc., Number 16, Perkins Translation 1, 1689–1693; Tetrahedron Letters, Number 33, 3099–3100). 2-Chloro-3-phytyl-1,4-naphthoquinone (chloro-$K_1$) was synthesized according to the method of Lowenthal and Chowdhury (Canad. J. Chem. 48, 3957–3958) with modifications described elsewhere (Pharmacology of Rat Heptatic Vitamin K-Dependent Carboxylation, Doctoral Dissertation, Duke University). All other reagents were at least analytical reagent grade and were from commercial sources.

Animals:

Adult male Sprague-Dawley rats (Crl:CD$^R$(SD)BR outbred rats, Charles River Co., Wilmington, Mass.)

weighing 200–450 g were housed individually in polycarbonate cages with raised-wire floors. They were allowed free access to water. Food pellets (Rat Chow 5012, Ralston Purina Co., Richmond, Ind.) were allowed ad libitum until a fasting period began 20 to 22 hours prior to the time of sacrifice. For in vitro studies, pharmacological vitamin K deficiency was induced approximately 19 hours prior to the time of sacrifice by intravenous (i.v.) administration (into a caudal vein during light ether anesthesia) of 2 mg/kg sodium warfarin (Annales Medicinae Experimentalis et Biologiae Fenniae 43 (Supp. 3), 1–99). This synthesis blocking dose of warfarin will produce plasma prothrombin complex activity at the time of sacrifice approximately equal to 6% of normal (Pharmacology of Rat Heptatic Vitamin K-Dependent Carboxylation, Doctoral Dissertation, Duke University). This pharmacological state of vitamin K deficiency has been fully characterized (Arch. Biochem. Biophys. 150, 91–95 and 191, 571–577) and it is comparable to dietary vitamin K deficiency, which demands a minimum of 10 days to produce (Proc. Soc. Exp. Biol. Med. 101, 467–468).

Vitamin K-Dependent Carboxylase Preparation:

The procedures for preparation of vitamin K-dependent carboxylase and assay of carboxylation were similar to those described in other laboratories (J. Biol. Chem. 251, 2770–2776; Biochim. Biophys. Acta 499, 181–193). Each animal was studied under both control and inhibitory conditions. The rats were rendered unconscious with nitrogen, the liver was quickly excised and minced in a total volume of 2.0 ml ice cold buffer I (0.25M sucrose, 0.025M imidazole, pH 7.20) per gram of liver. The liver was homogenized using 4 passes of a Teflon pestle (clearance 0.15–0.23 mm; Arthur H. Thomas Co., Philadelphia, Pa.) at 300 rpm. The post-mitochondrial supernatant and microsomal pellet were prepared by a published procedure (J. Biol. Chem. 251, 2770–2776). The microsomal pellet was resuspended in buffer II (0.25 M sucrose, 0.025M imidazole, 0.080M KCl, pH 7.20). This suspension supplied both the enzymes (vitamin K-dependent carboxylase and enzymes for vitamin K biotransformations) and endogenous substrates (precursors of vitamin K-dependent proteins) of interest. Microsomal suspension protein concentration was determined by the method of Bradford (Anal. Biochem. 72, 248–254) as described for Bio-Rad reagent and adjusted to approximately 15 mg/ml in buffer II.

Assay of Vitamin K-Dependent Carboxylation:

Control, blank, and experimental reaction mixtures were made for each experiment. Control and blank reaction mixtures were made up with vitamin K and without vitamin K, respectively. Experimental reaction mixtures contained both vitamin K and a vitamin K antagonist. The control reaction mixture contained 3.00 ml of microsomal suspension, 0.81 ml of buffer II, 1.20 ml of an ATP-generating system (final concentrations: 1 mM ATP, 10 mM phosphocreatine, 2.5 mM Mg[acetate]$_2$·4H$_2$O, 20 µg/ml creatine phosphokinase [52 U/ml]), 0.60 ml of NADH (final concentration 2 mM), 0.30 ml of dithiothreitol (final concentration 7 mM) dissolved in buffer II, 0.060 ml of NaH$^{14}$CO$_3$ (1.0 µCi/µl; added 0.5 min prior to reaction initiation), and at the time of reaction initiation 0.030 ml of vitamin K$_1$ (final concentration 20 µg/ml) diluted in 0.85% sodium chloride solution. This vitamin K concentration is associated with maximal in vitro incorporation of added H$^{14}$CO$_3$ into vitamin K-dependent substrate proteins (J. Biol. Chem. 251, 2770–2776). The blank reaction mixture consisted of the same components except that vitamin K was replaced by an equal volume of isotonic saline. The experimental reaction mixtures were made up in the same way as the control reaction mixtures with the exceptions that: (1) a volume of buffer II was replaced by a volume of buffer II containing an inhibitor of vitamin K-dependent carboxylation, and (2) all individual volumes were two-thirds of those in the control reaction mixtures. The sodium salts of TCP, phenindione, and warfarin were formed in aqueous sodium hydroxide solution (J. Am. Chem. Soc. 83, 2676–2679) and were freely soluble in buffer II at all concentrations used in these studies. Chloro-K$_1$ was formulated as an oil-in-water emulsion with Tween 80 (5% v/v final concentration), while chloro-K$_3$ was formulated as a suspension in Tween 80 (5% v/v final concentration) (Molecular Pharmacology 10, 373–380).

Reaction mixtures were incubated for 5 minutes at 100 excursions per minute in a reciprocating shaker water bath at 27°. After addition of vitamin K or saline, serial samples (0.45 ml each) were collected from each control and blank reaction tube at 2, 4, 6, 8, 10, 12, 14, 16, 30, 60, 90, and 120 minutes, and from each experimental reaction tube at 2, 4, 6, 8, 10, 12, 14, and 16 minutes. Each 0.45 ml sample was transferred to a tube containing 1 ml of ice-cold 10% TCA. The TCA-precipitated $^{14}$C-containing protein pellet was then prepared as previously described (J. Biol. Chem. 251, 2770–2776) and radioactivity was determined in an Intertechnique (Plaisir, France) liquid scintillation spectrometer using the external standard method of quench correction.

Analysis of Carboxylation Data:

Vitamin K-dependent carboxylation in each subsample was calculated as the dpm $^{14}$C incorporated per mg microsomal protein (dpm/mg) for the vitamin K-containing reaction tube of interest minus the dpm/mg for the corresponding blank reaction tube. The time course of vitamin K-dependent carboxylation over the 2 hour observation period was well described by the first-order monoexponential function $P = P_\infty(1 - \exp[-Kt])$ where Marquardt's nonlinear regression algorithm (SIAM J. 11, 431–441) was used to estimate the parameters K and $P_\infty$. In this equation, K is a first-order rate constant, t is incubation time, P is dpm/mg of vitamin K-dependent carboxylation, and $P_\infty$ is the asymptotic value of P. Consistent with observations in the rat, bovine, and equine vitamin K-dependent carboxylation systems, (Arch. Biochem. Biophys. 191, 571–577; Biochim. Biophys. Acta 714, 361–365; Thromb. Res. 28, 171–177), $P_\infty$ is the maximum amount of endogenous substrate available for in vitro vitamin K-dependent carboxylation.

Since vitamin K-dependent carboxylation is unsaturated with respect to its endogenous substrate for the rat hepatic carboxylase preparation (alluded to in Arch. Biochem. Biophys. 191, 571–577 and Biochem. Biophys. Res. Commun. 86, 500–507), the kinetics of endogenous substrate carboxylation under the reaction conditions described are apparently first-order. This kinetic order is indicated by the linear appearance of a plot according to the substrate-limiting form of the integrated Michaelis-Menten equation (Methods in Enzymology 63, 159–183), i.e., $\ln(P_\infty[P_\infty - P])$ versus t. The slope of this product accumulation rate plot is equal to $V/K_M$ (Methods in Enzymology 63, 159–183). Values of $V/K_M$ are reported in units of minutes$^{-1}$, while values of $P_\infty$ are reported in dpm/mg. Normalized $P_\infty$ values were calculated by dividing by the quantity of microsomal protein harvested for the individual rat in order to adjust for interanimal differences in liver weight and yield of microsomal protein. The percentage inhibition of vitamin K-dependent carboxylation was calculated as the percentage decrease in the slope of the product accumulation rate plot from the control slope, with each slope calculated by linear least-squares regression with the y-intercept equal to zero.

Concentration-response relationships were calculated by fitting the percent inhibition (I) versus inhibitor concentration (C) data for each individual animal with the logistic function (Amer. J. Physiol. 235, E97-E102):

$$I = \frac{I_0 - I_{Max}}{1 + \left(\frac{C}{IC_{50}}\right)^s} + I_{Max}$$

where $I_O$ is the percent inhibition when $C = 0$, $I_{Max}$ is the maximum attainable percent inhibition, $IC_{50}$ is the concentration of inhibitor associated with 50% inhibition, and s is the slope parameter. This nonlinear regression was performed using Marquardt's algorithm (SIAM J. 11, 431-441) with a Tektronix 4052 computer (Beaverton, Oreg.).

In vivo Studies:

Studies were conducted to elucidate possible relationships between in vitro rates of vitamin K-dependent carboxylation and in vivo rates of prothrombin complex activity (PCA) synthesis and steady-state levels of PCA. In view of the relatively small range of values of the in vitro intrinsic formation rate of carboxylated vitamin K-dependent proteins ($V/K_M$) in 40 normal rats [quartile range = 0.0896 to 0.1234 minutes$^{-1}$ (Pharmacology of Rat Heptatic Vitamin K-Dependent Carboxylation, Doctoral Dissertation, Duke University)], it was anticipated that a relationship between this parameter and the in vivo rate of PCA synthesis could only be elucidated over a reasonably broad range of values of $V/K_M$ if this relationship was studied in normal rats and in rats with hepatic dysfunction. Hepatic dysfunction was produced by chemical means using ANIT and carbon tetrachloride, both of which are known hepatotoxins and acutely decrease the activity of vitamin K-dependent clotting factors in rats (Toxicol. Appl. Pharmacol. 48, 445-458; Amer. J. Hematol. 8, 249-255). In addition, treatment with phenobarbital, which is a known hepatic microsomal enzyme inducer and has been reported to elevate the activity of circulating vitamin K-dependent factors in rats (Life Sciences 26, 1379-1383), was used in an effort to enhance the rates of both the in vitro and in vivo reactions. After these pretreatments, the animals were administered a synthesis blocking dose of warfarin to define the in vivo parameters of PCA and subsequently sacrificed to determine the in vitro parameters of hepatic vitamin K-dependent carboxylation.

A single 150 mg/kg does of ANIT was administered intraperitoneally (i.p.) to rats by injecting a volume of 4 ml/kg of a solution of 37.5 mg/ml ANIT in corn oil at 48 hours prior to the administration of warfarin. Other rats received a single dose (either 0.5 or 1.0 ml/kg) of carbon tetrachloride dissolved in corn oil (10 ml/kg of a 5% or 10% v/v solution) i.p. (Biochem. Pharmacol. 18, 2019-2027). The single CCl$_4$ dose was administered either 14 or 24 hours prior to administration of warfarin. Animals pretreated with phenobarbital received four daily doses of 100/mg/kg administered i.p. dissolved in 0.85% sodium chloride solution (2 ml/kg of a 50 mg/ml solution). Sodium warfarin 2 mg/kg was injected i.v. into one of the caudal veins following dissolution in 0.85% sodium chloride to yield a final concentration of 1 mg/ml.

Blood samples were collected by serial percutaneous puncture of the caudal artery over a period of up to 12 hours, anticoagulated with sodium oxalate and centrifuged immediately at 1,500 ×g for 15 minutes at 2°-4° (J. Pharmacol. Exp. Ther. 184, 253-260). The supernatant plasma was aspirated into an ice-cooled polypropylene tube for immediate determination of prothrombin time.

Determination of Prothrombin Complex Activity:

Plasma PCA was determined from prothrombin time measurements (J. Pharmacol. Exp. Ther. 184, 253-260). Prothrombin time (PT) was determined by adding 200 μl of a standard solution of thromboplastin, Factor V, and fibrinogen (Simplastin-A, General Diagnostics, Morris Plains, N.J.) maintained at 37° to 100 μl of an appropriate plasma dilution using a Fibrometer coagulation timer (BBL, Cockeysville, Md.). All samples were measured in duplicate. A pooled animal standard curve relating PT and PCA was constructed as described previously (J. Pharmacol. Exp. Ther. 184, 253-260 and 201, 507-517). The baseline relationship between PT and PCA was linear according to the function, $PT = a + m(1/PCA)$, where the values of the parameters a and m were calculated by linear least-squares regression. This pooled animal standard curve was used to calculate PCA°, i.e., the steady-state value of PCA determined immediately prior to warfarin administration.

A similar procedure was used for each individual rat to construct a standard curve relating PT and PCA for plasma collected prior to warfarin administration. Each individual animal standard curve was used to calculate the PCA values obtained at different times in the individual rat for determination of the apparent first-order rate constant ($k_d$) for degradation of PCA after warfarin administration. Values of PCA° and $k_d$ were used to calculate the steady-state rate of PCA synthesis before warfarin administration as $R°_{Syn} = PCA° \times k_d$ (Life Sciences 26, 1379-1383; Acta Haemat. 19, 20-29; Clin. Pharmacol. Ther. 10, 22-35).

Correlation of in vivo and in vitro Activities:

After completion of the in vivo studies, in vitro determinations of parameters of hepatic microsomal vitamin K-dependent carboxylation were begun. Each animal was sacrificed approximately 22 hours after administration of the synthesis blocking dose of warfarin, and the parameters $V/K_M$ (intrinsic formation rate) and $P_\infty$ (amount of precursors available for carboxylation) of hepatic microsomal vitamin K-dependent carboxylation were determined as before. To discern the presence of relationships between parameters of in vivo vitamin K-dependent hemostatic function and in vitro parameters of vitamin K-dependent carboxylation, scatter plots were made and inspected. The degree of concordance between variables was quantified as Kendall's $\tau_b$ correlation coefficient (Rank Correlation Methods, 34-93), while the degreee of linear correlation between variables was quantified as Pearson's product-moment correlation coefficient (r).

Figure 1B:
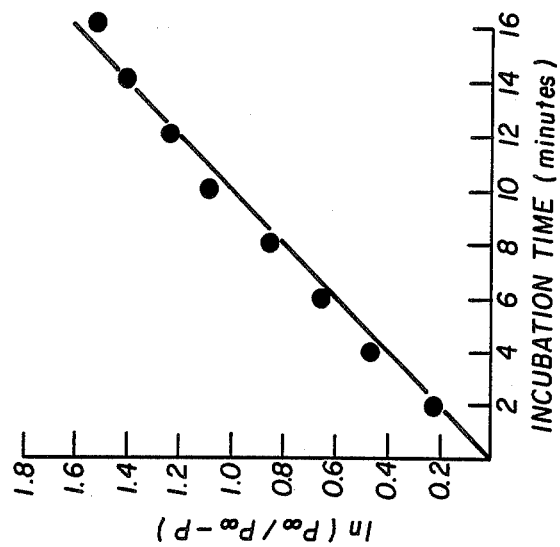
Figure 1C:
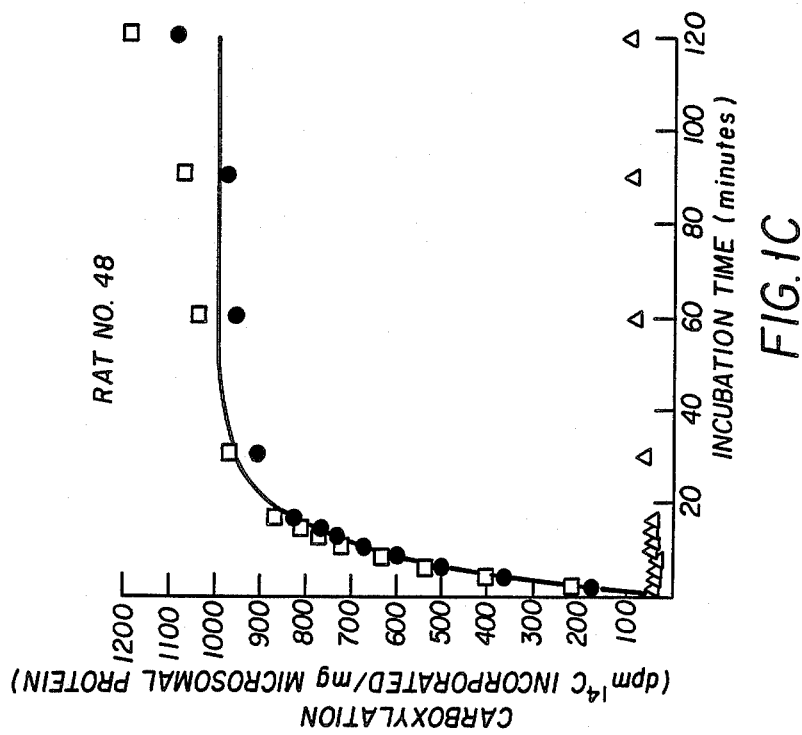
Figure 2B:
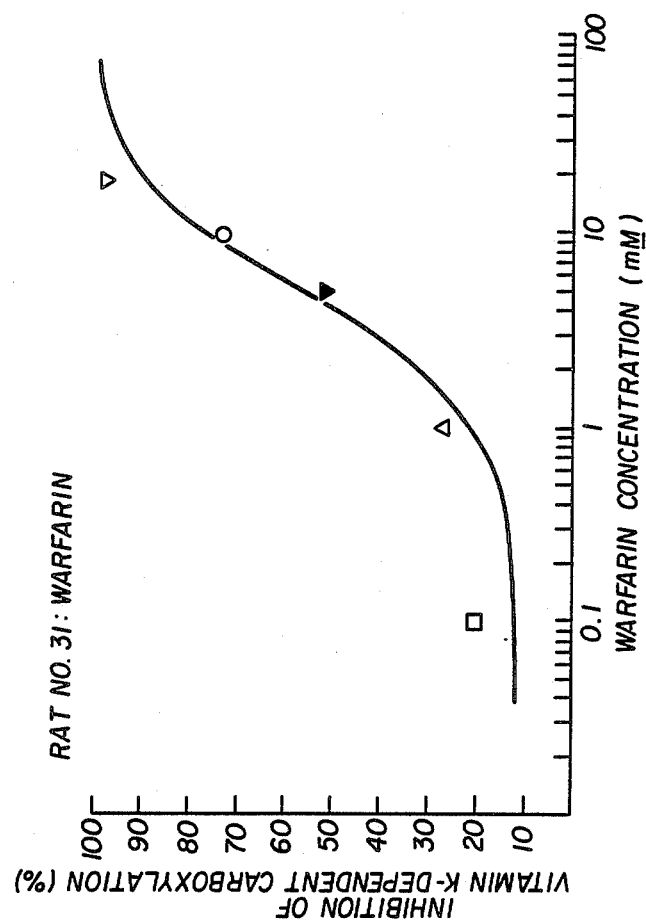
FIG. 2. Generation of percent in vitro inhibition of vitamin K-dependent carboxylation versus inhibitor concentration relationships for warfarin in rat #31 (upper panel) and 2,6-dichloroindophenol sodium in rat #35 (lower panel). Left side graphs illustrate the diminishing slopes (i.e., increasing degrees of inhibition) of the product accumulation rate plots with increasing concentration of inhibitor. The linear least-squares regression lines are shown. Right side graphs (with corresponding symbols) show the resulting percent inhibition versus concentration plots. The nonlinear least-squares regression curves are superimposed. Note that the control (●) points are not plotted in the right side graphs.
Figure 2A:
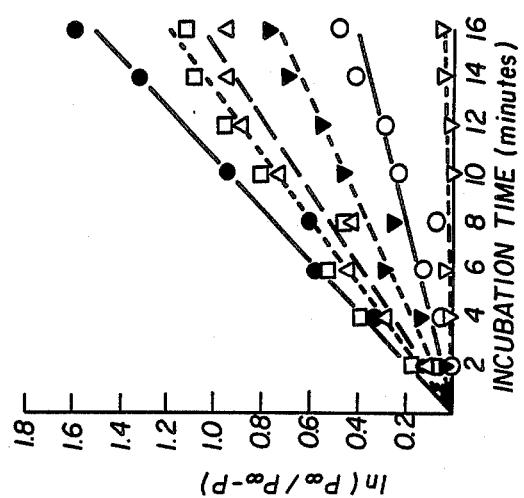
Figure 2D:
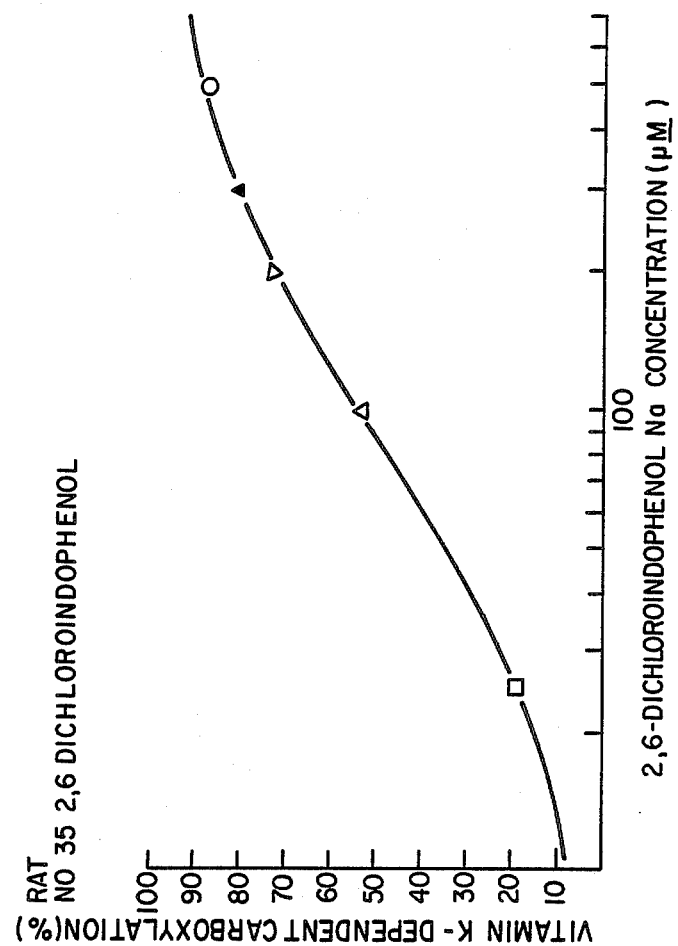
Figure 2C:
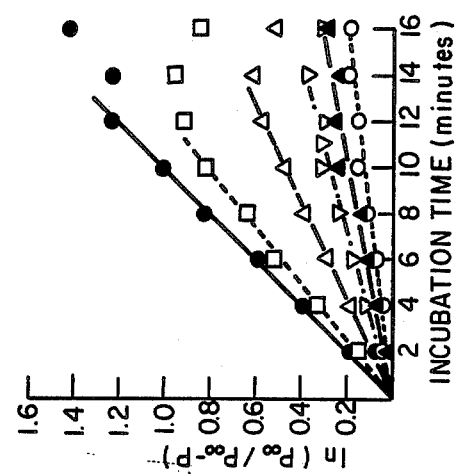
Figure 3A:
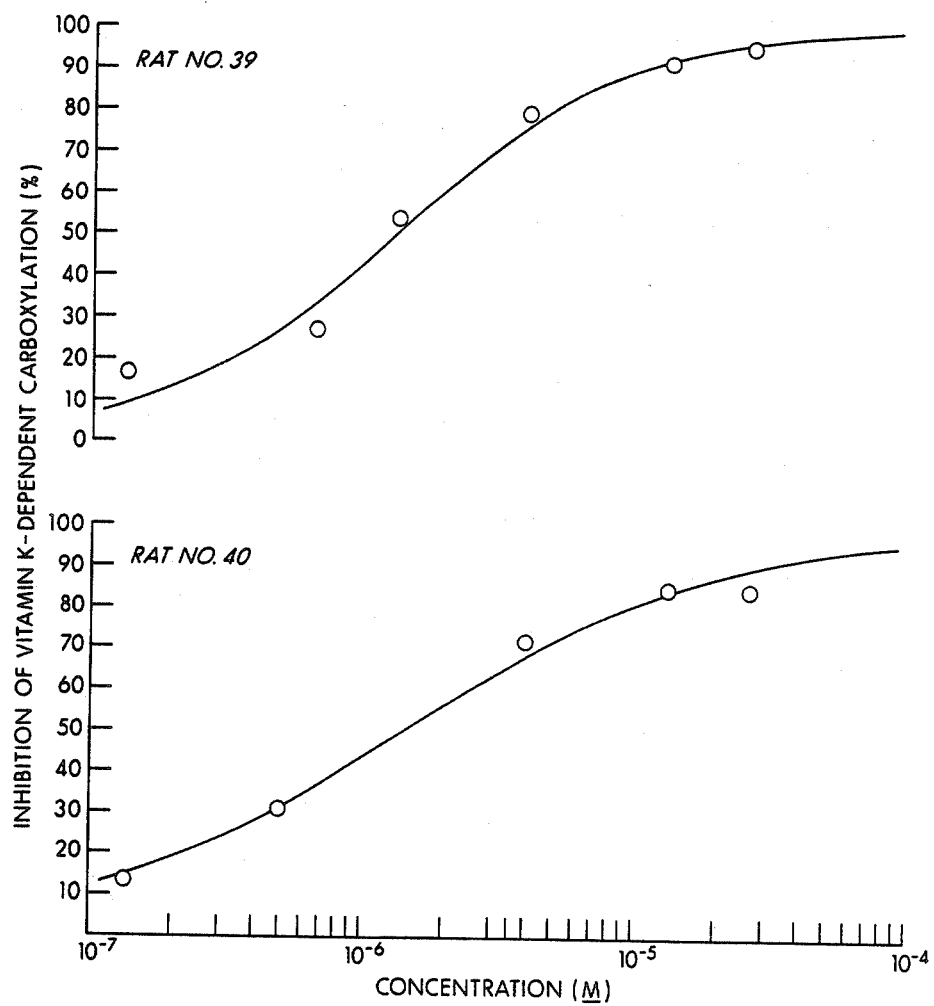
FIG. 3. Relationship between in vitro inhibition of vitamin K-dependent carboxylation and concentration of six vitamin K antagonists. The antagonists studied were 2,3,5,6-tetrachloropyridin-4-ol, phenindione, 2,6-dichloroindophenol sodium, 2-chloro-1,4-naphthoquinone, 2-chloro-3-phytyl-1,4-naphthoquinone, and warfarin. Shown are two representative curves for each inhibitor. The nonlinear least-squares regression curves are superimposed.
Figure 3B:
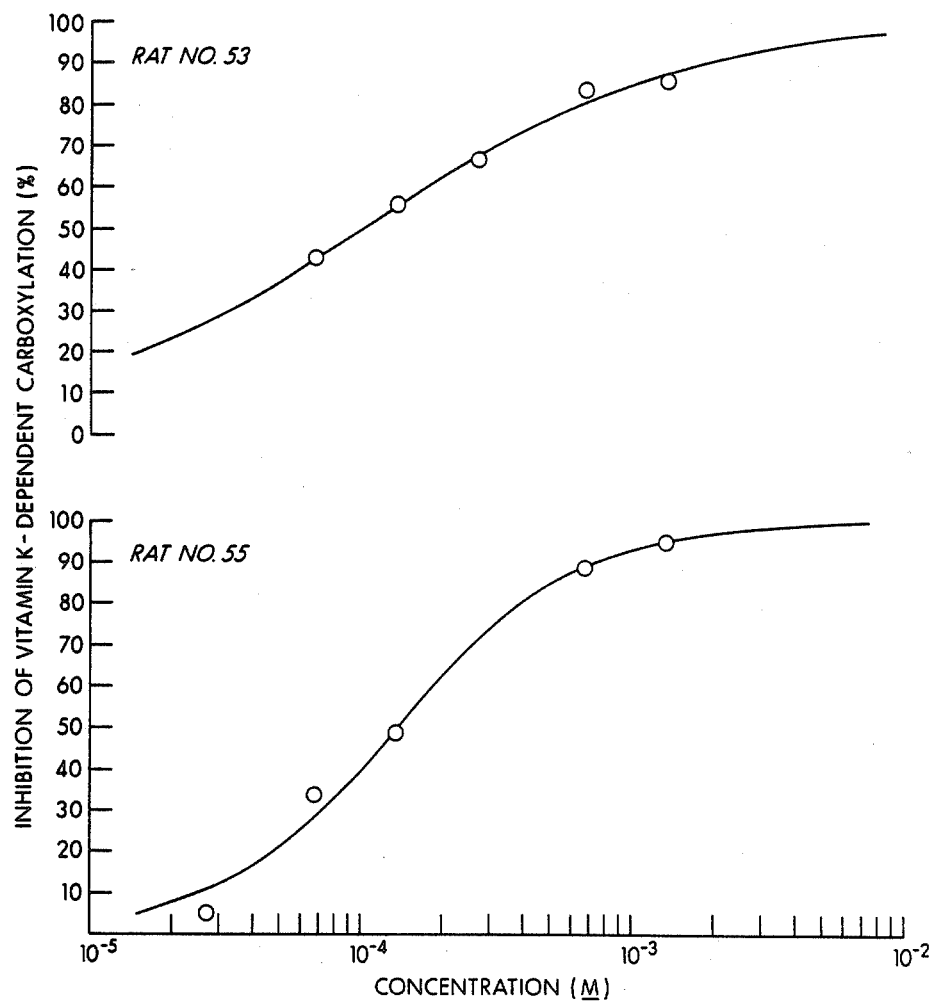
Figure 3C:
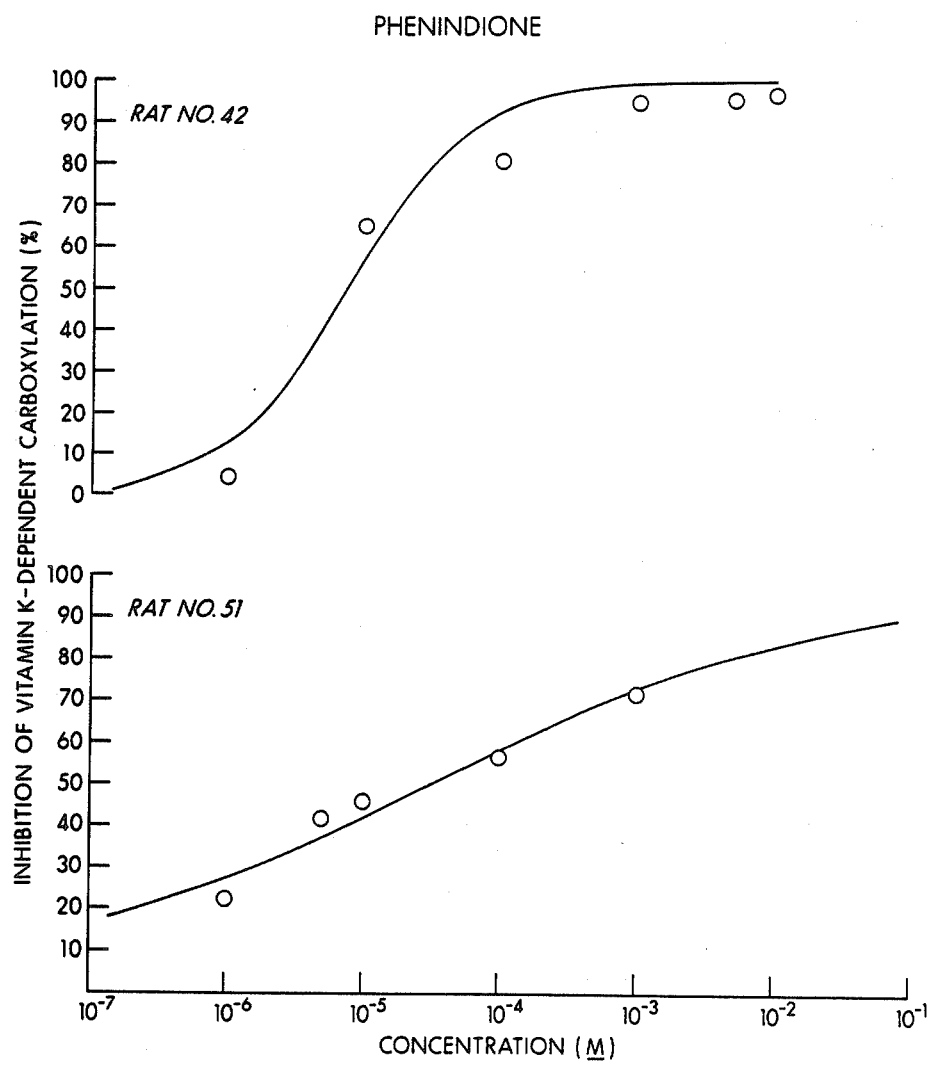
Figure 3D:
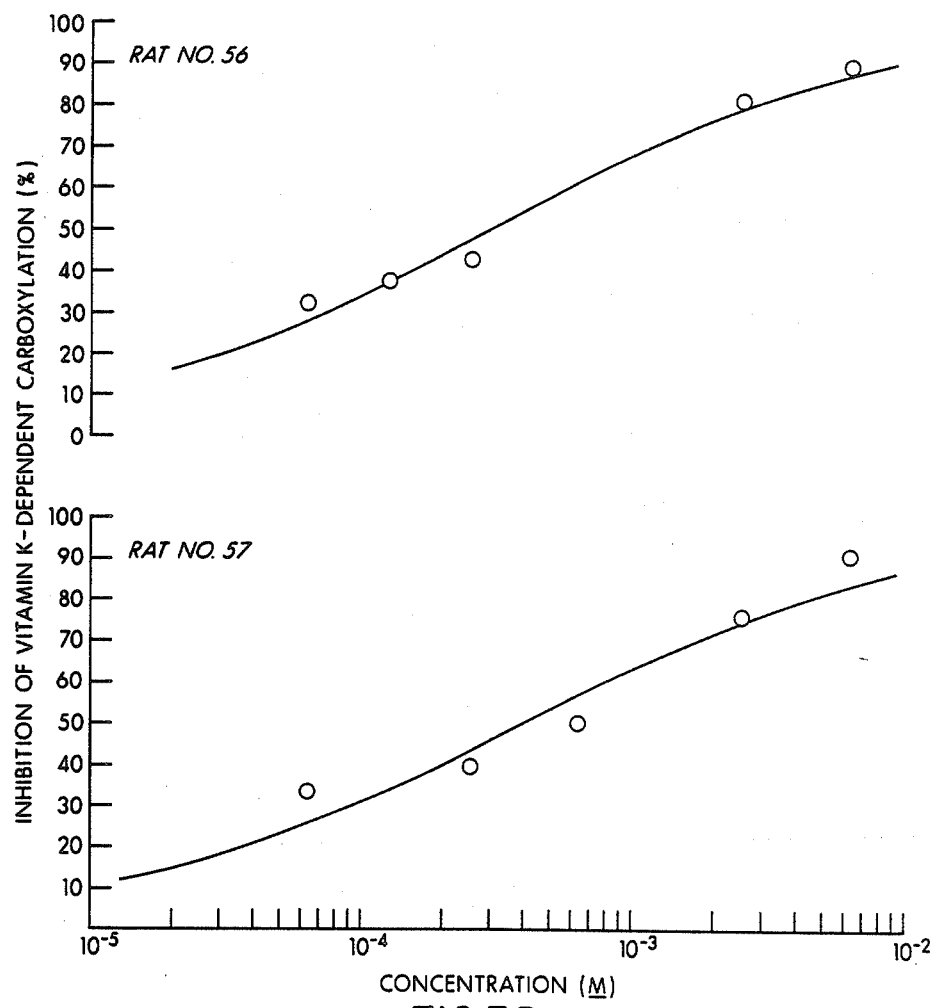
Figure 3E:
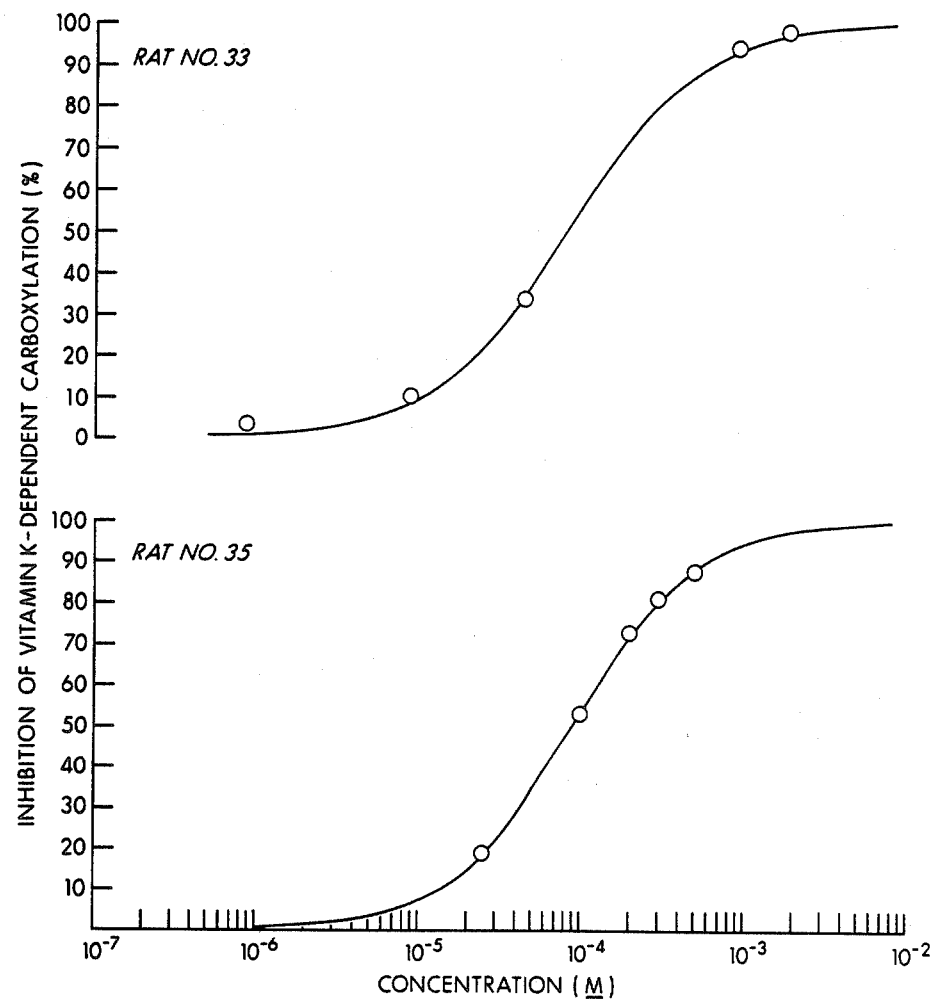
Figure 3F:
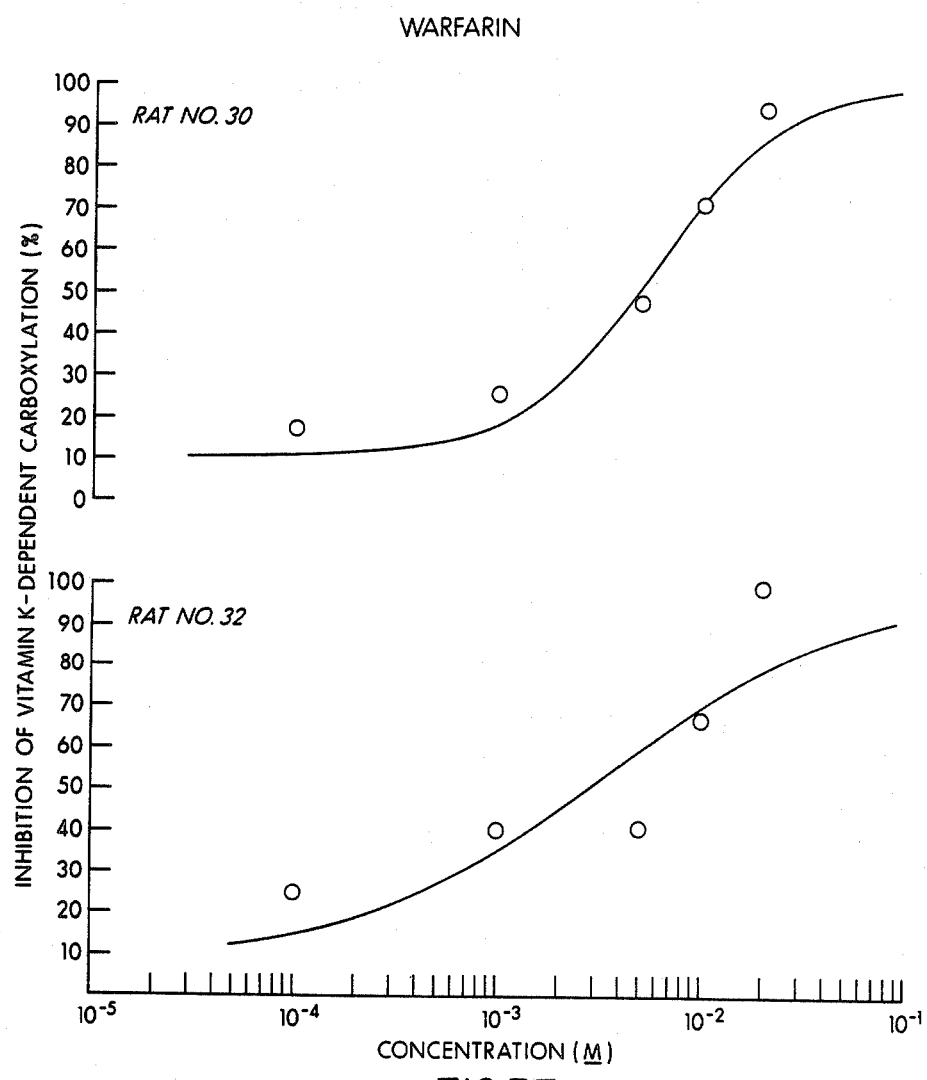

Vitamin K-Dependent Carboxylation:

The time course of vitamin K-dependent carboxylation was determined for each rate (FIG. 1, left side graphs). Estimation of the K and $P_\infty$ parameters of this equation proved to be very accurate as reflected by the low coefficients of variation (C.V.) for K (8.97% ±3.88%, mean C.V. ±S.D., n=40) and $P_\infty$ (3.01% ±1.16%). The average $P_\infty$ value was 1,611±498 dpm/mg. Following estimation of $P_\infty$, the time course of vitamin K-dependent carboxylation was plotted according to the product accumulation rate equation (FIG. 1, right side graphs). The slope ($V/K_M$) of this plot, which is the same as K in the monoexponential equation, was calculated via linear least-squares regression analysis. The rationale for using the slope values from the product accumulation rate equation rather than the ones from the monoexponential equation was that the former method offered a more convenient way to compute changes in the slope values in the presence of antagonists. This method of data analysis has proven to be quantitatively reproducible across a series of 40 normal rats. The average slope of the product accumulation rate plot was 0.1074 ±0.0289 minutes$^{-1}$ (mean ±S.D.; 28 of 40 r values≧0.990; 38 of 40 r values≧0.900; minimum r value=0.875).

Effects of Inhibitors of Vitamin K-Dependent Carboxylation:

Data for the time course of vitamin K-dependent carboxylation in the absence and presence of six different antagonists were plotted according to the product accumulation rate plot (FIG. 2, left side graphs). The percentage decrease in slope from the control slope is equal to the percentage inhibition of vitamin K-dependent carboxylation. This enabled the construction of percent inhibition versus concentration plots (FIG. 2, right side graphs). Such plots were constructed for individual rats treated in vitro with TCP, phenindione, 2,6-DIP, chloro-$K_3$, chloro-$K_1$, or warfarin. FIG. 3 shows two representative percent inhibition versus concentration plots for each of these six inhibitors.

With the exception of warfarin, the percent inhibition versus concentration plots exhibited a classical sigmoidal shape and were well described by the logistic function where $I_o$ and $I_{Max}$ were fixed at 0% and 100%, respectively. The $IC_{50}$ and s parameter values were estimated well by the nonlinear least-squares regression procedure as indicated by the relatively low mean coefficient of variation for the $IC_{50}$ (16.9%±13.6%, mean C.V.±S.D., n=21) and s (12.3 ±8.3%) parameters. Compared with these well characterized sigmoidal relationships, the percent inhibition versus concentration plots for warfarin were a typical in two respects: first, the need to use $I_o$ as a parameter (final value significantly greater than 0) to obtain the best fit with the logistic equation (average $I_o$ was 8.9%); and second, the lack for some rats of a clear inflection point in the percent inhibition versus concentration plots. Possible explanations for this behavior are discussed below.

Figure 4:
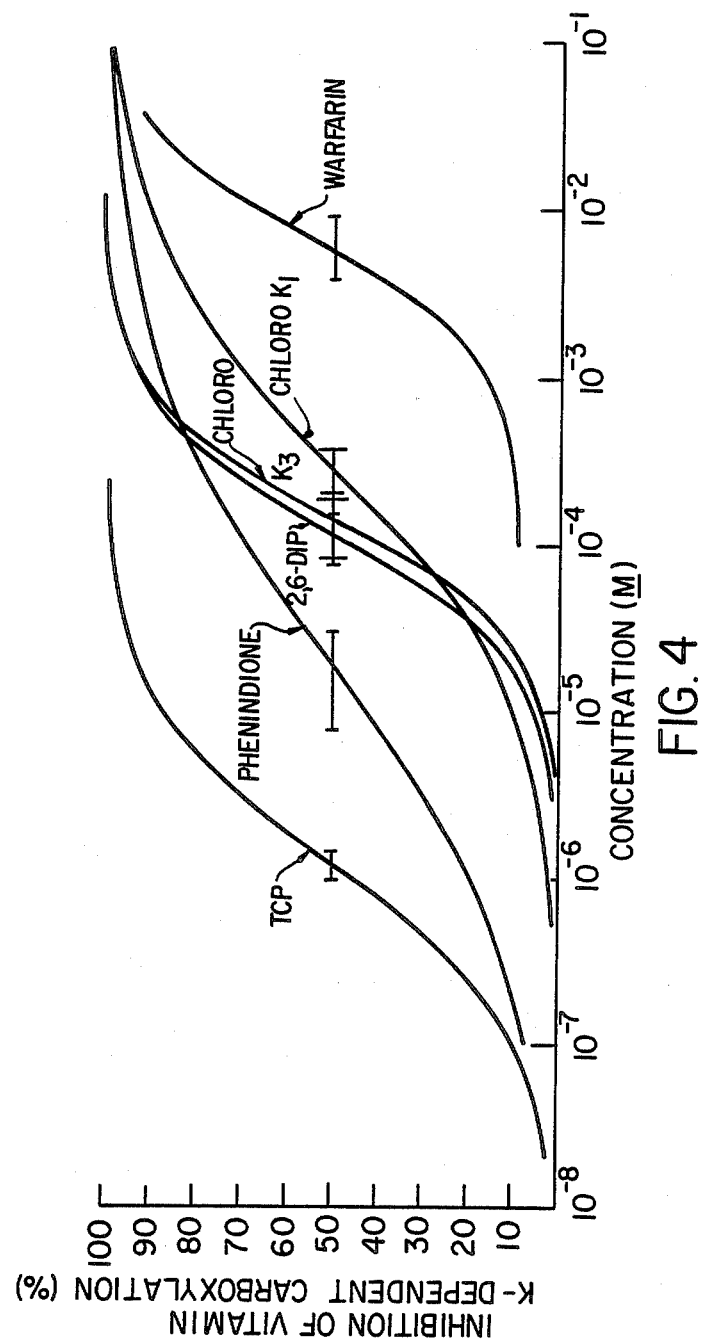
FIG. 4. Comparative summary of percent in vitro inhibition of vitamin K-dependent carboxylation versus inhibitor concentration relationships for 2,3,5,6-tetrachloropyridin-4-ol (TCP), phenindione, 2,6-dichloroindophenol sodium (2,6-DIP), 2-chloro-1,4-naphthoquinone (chloro-$K_3$), 2-chloro-3-phytyl-1,4naphthoquinone (chloro-$K_1$), and warfarin (listed in decreasing order of potency). Curves were generated from the mean parameters given in Table I. The horizontal bars indicate the mean ± S.D. for each $IC_{50}$, where the dotted bars pertain to chloro-$K_3$ and the taller bars pertain to chloro-$K_1$.

The parameters of the percent inhibition versus concentration relationships are summarized in Table I and illustrated in FIG. 4.

TABLE I

Summary of $IC_{50}$ and slope parameters characterizing the percent inhibition of vitamin K-dependent carboxylation versus inhibitor concentration relationships. Values are the mean ± S.D.; values in parentheses are the ranges.

| Inhibitor | Number of Animals | $IC_{50}$ (μm) | Slope (% Inhibition/Concentration) |
|---|---|---|---|
| TCP | 4 | 1.23 ± 0.24 (0.89–1.44) | 0.884 ± 0.117 (0.734–1.02) |
| Phenindione | 4 | 19.0 ± 11.2 (7.36–30.2) | 0.475 ± 0.330[b] (0.269–0.963) |
| 2,6-DIP | 4 | 116 ± 39.2 (78.1–160) | 1.13 ± 0.174 (0.940–1.36) |
| Chloro-$K_3$ | 4 | 146 ± 62.1 (100–236) | 1.20 ± 0.340 (0.738–1.55) |
| Chloro-$K_1$ | 5 | 285 ± 89.3 (171–393) | 0.634 ± 0.159[b] (0.469–0.898) |
| Warfarin[c] | 6 | 6.63 ± 2.85 (3.46–10.8) | 1.29 ± 0.577 (0.637–2.20) |

[a]All concentrations are μM, except warfarin is mM.
[b]Slope significantly different from 1 by 2-tailed Students t-test. Phenindione slope: p = 0.05. Chloro-$K_1$ slope: 0.001 < p < 0.01.
[c]Function fit using $I_O$ as a third parameter with final value = 8.89 ± 3.77% (mean ± S.D.; range = 2.74–13.1%). Coefficients of variation for parameters $IC_{50}$: 43.1% ± 26.0%, mean C.V. ± S.D.; n = 6; s: 41.8% ± 12.3%, mean C. V. ± S.D., n = 6.

The $IC_{50}$ values for these compounds are ranked by increasing $IC_{50}$ as TCP, phenindione, 2,6-DIP, chloro-$K_3$, chloro-$K_1$, and warfarin. The slope parameter was essentially no different from 1 for four antagonists; however, the slope was significantly less than 1 for phenindione (p=0.05) and chloro-$K_1$ (0.001<p 0.01). The large magnitude of interinhibitor variation in $IC_{50}$ was evident in the approximately 5,000-fold difference between the $IC_{50}$ of the most potent (TCP) and least potent (warfarin) compound. For each compound, the 2- to 4-fold range of $IC_{50}$ values among rats was illustrative of the magnitude of the observed interindividual difference in the in vivo anticoagulant response to warfarin, phenindione, and TCP in the rat (J. Pharmacol. Exp. Ther. 201, 507–517; Proc. Soc. Exp. Biol. Med. 139, 806–810; Scand. J. Clin. Lab. Invest. 2, 83–91).

Figure 5:
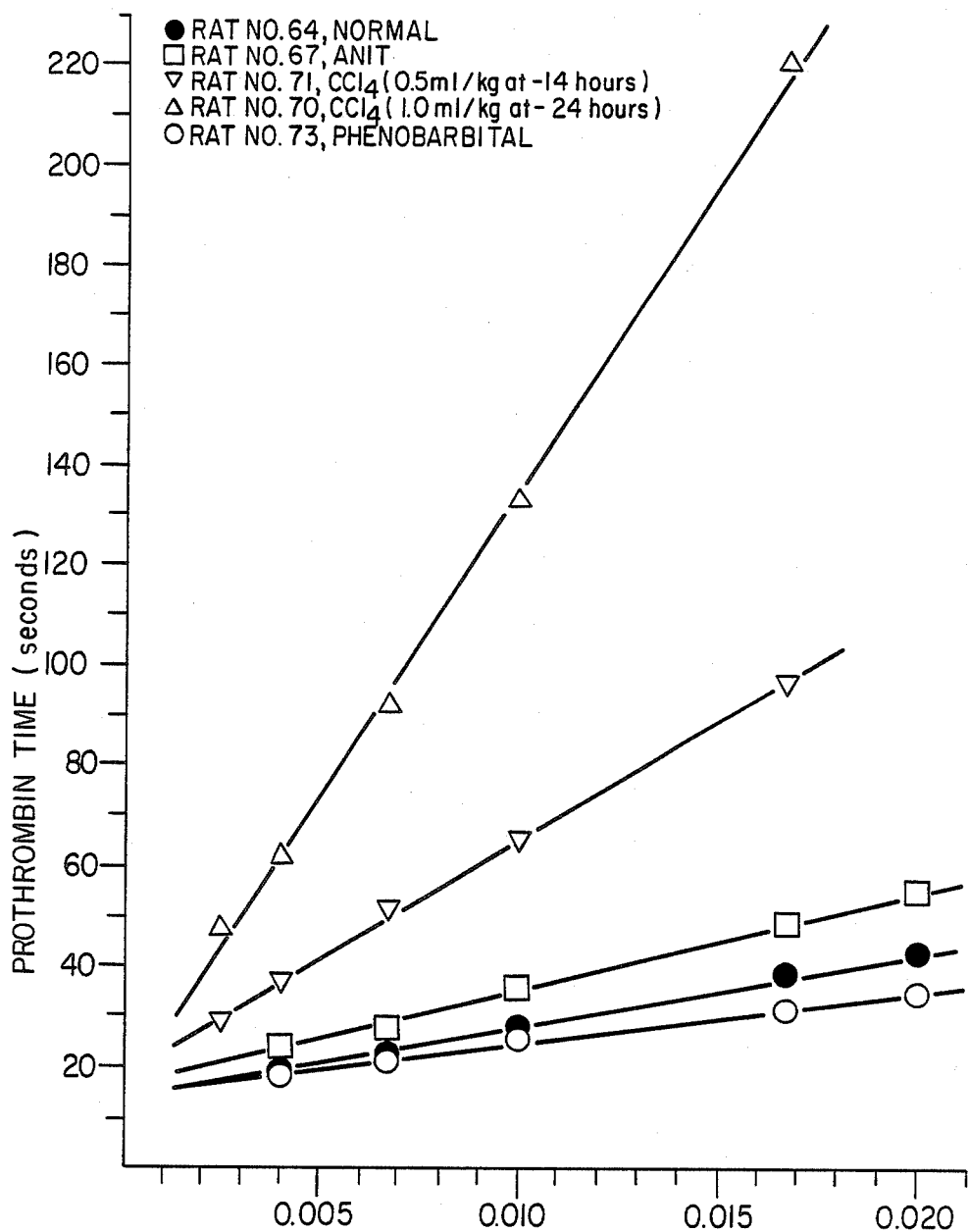
FIG. 5. Individual animal standard curves relating to prothrombin time to prothrombin complex activity in normal, ANIT-pretreated, carbon tetra-chloride-pretreated, and phenobarbital-pretreated rats. The respective linear least-squares regression lines are superimposed (all r values>0.990).

In Vivo Studies:

For animals studied in vivo, the pooled animal and individual animal standard curves relating PT to PCA were well described by the inverse function equation for normal rats, an ANIT-treated rat, carbon tetra-chloride-treated rats, and phenobarbital-treated rats (FIG. 5). Although the intercept parameter did not differ markedly among rats receiving these various pretreatments, the slope parameter exhibited considerable interanimal variability among normal rats and marked pretreatment-related changes in slope, as shown in Table II and FIG. 5.

TABLE II

Parameters of individual animal standard curves and values of PCA°, $k_d$, and $R°_{Syn}$

| Treatment | Animal No. | a (sec) | m (%/sec) | PCA° (%) | $k_d$ (Day$^{-1}$) | $R°_{Syn}$ (%/day) |
|---|---|---|---|---|---|---|
| Control | 63 | 14.0 | 1,095 | 96.7 | 3.14 | 304 |
| | 64 | 13.9 | 1,396 | 87.4 | 4.33 | 378 |
| | 65 | 15.6 | 1,310 | 77.0 | 3.13 | 241 |
| | 66 | 13.1 | 1,401 | 94.4 | 4.25 | 401 |
| ANIT | 67 | 16.0 | 1,868 | 56.1 | 2.76 | 155 |
| $OCl_4$ | 69 | 14.2 | 7,037 | 16.9 | 5.98 | 101 |
| | 70 | 12.9 | 12,282 | 9.9 | 13.90 | 137 |
| | 71 | 17.1 | 4,701 | 23.4 | 5.89 | 137 |
| Phenobarbital | 72 | 14.0 | 1,327 | 143.1 | 3.72 | 533 |
| | 73 | 14.9 | 947 | 102.7 | 4.12 | 423 |

Carbon tetrachloride, the more severe hepatotoxin tested, was associated with the largest increases in slope. A smaller increase in slope occurred in the ANIT-treated rat.

Figure 6:
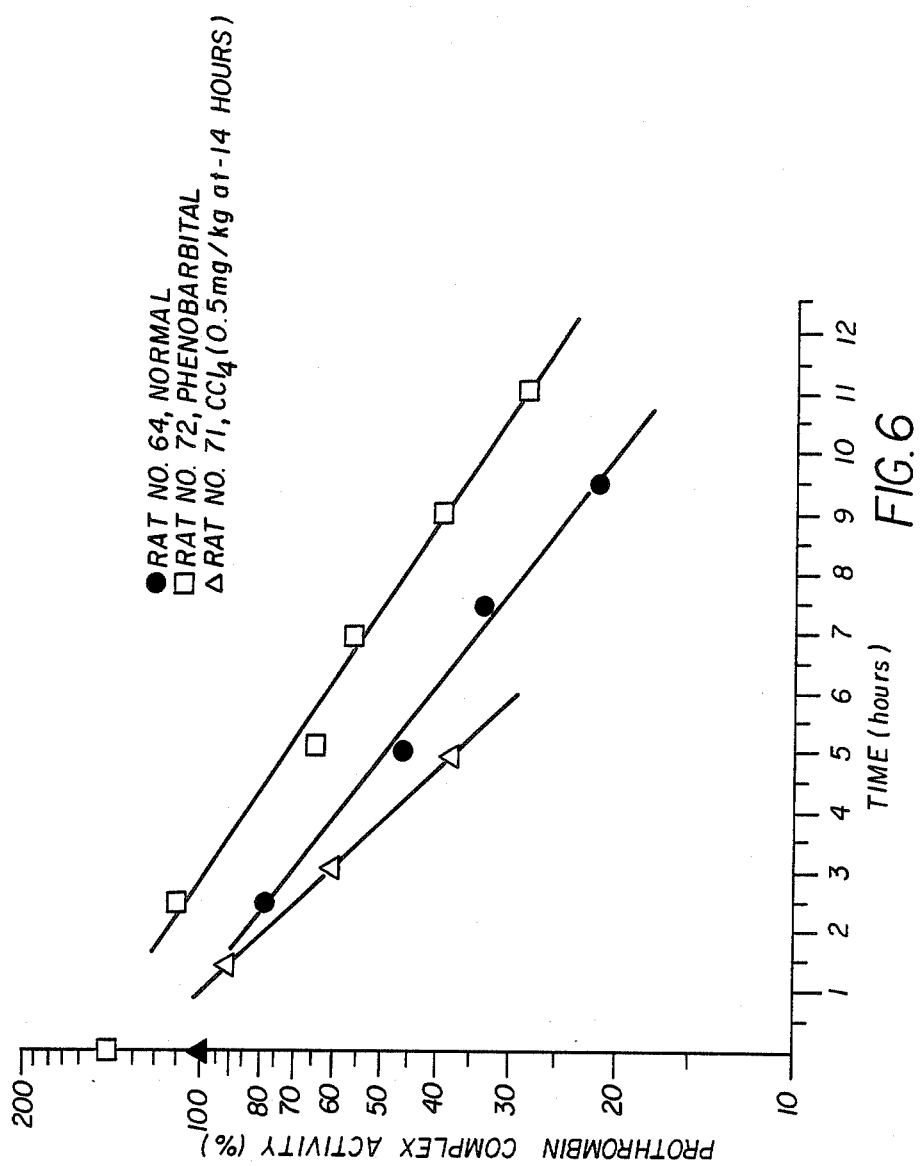
FIG. 6. Determination of first-order rate constant for degradation of prothrombin complex (PCA) in normal, carbon tetrachloride-pretreated, and phenobarbital-pretreated rats. The respective linear least-squares regression lines are superimposed (absolute values of all r values>0.990).

Previous investigators have demonstrated apparent first-order kinetics of degradation of PCA following administration of a synthesis blocking dose of warfarin or dicumarol in rats (J. Pharmacol. Exp. Ther. 184, 253-260; 201, 507-517; and 187, 176-184). This finding was verified here in normal rats (FIG. 6, Table II). The average $k_d$ for PCA in normal rats was 3.71 ±0.67 day$^{-1}$ corresponding to an average turnover time of 6.63 ±1.19 hours and a biologic half-life of 4.59 ±0.83 hours. Apparent first-order kinetics were also observed in the presence of hepatic dysfunction of a cholestatic nature (associated with ANIT pretreatment) and a hepatocellular nature (associated with carbon tetrachloride pretreatment) (Table II). The rate constants for degradation of PCA were quantitatively similar in normal rats, phenobarbital-treated rats, and the ANIT-treated rat (Table II) In contrast, carbon tetrachloride-treated rats had markedly increased values of $k_d$ (Table II), averaging 8.49±4.69 day$^{-1}$, corresponding to an average turnover time of 3.27±1.34 hours and a biologic half-life of 2.27±0.94 hours. This observation is consistent with the relatively dominant hepatic catabolic state and markedly depressed rate of hepatic microsomal protein synthesis in carbon tetrachloride-treated rats (Science 140, 308-310; Biochemistry 4, 671-679). There was a signifiant negative relationship between PCA° and $k_d$ (0.001 <P<0.05).

The rate of synthesis of PCA ($R°_{Syn}$) was derived from the observed parameters PCA° and $k_d$ (Table II). The values of $R°_{Syn}$ obtained in the normal rats, averaging 331±73%/day, were consistent with previously reported values (J. Pharmacol. Exp. Ther. 184, 253-260; 201, 507-517; and 187, 176-184). The two phenobarbital-treated rats had an average 38% increase beyond the average PCA° value in four normal rats, with essentially normal values of $k_d$, resulting in an average 44% increase in $R°_{Syn}$ beyond that in normal rats, as shown in Table III.

TABLE III

Parameters of in vitro vitamin K-dependent carboxylation in control, ANIT-pretreated, carbon tetrachloride-pretreated and phenobarbital-pretreated rats after evaluation of in vivo vitamin K-dependent hemostatic function.

| Treatment | Animal No. | $V/K_M$ (min$^{-1}$) | Normalized $P_\infty$ (dpm $^{14}$C incorporated/mg protein in sub-sample) |
|---|---|---|---|
| Control | 63 | 0.1218 | 9.32 |
| | 64 | 0.1239 | 10.16 |
| | 65 | 0.1170 | 9.58 |
| | 66 | 0.1563 | 10.35 |
| ANIT | 67 | 0.1104 | 15.59 |
| CCl$_4$ | 69 | 0.0798 | 6.58 |
| | 70 | 0.0944 | 9.86 |
| | 71 | 0.1257 | 9.04 |
| Phenobarbital | 72 | 0.1174 | 4.92 |
| | 73 | 0.1586 | 5.86 |

This percentage increase in $R°_{Syn}$ is somewhat greater than the observed 26% increase in fractional liver weight (i.e., liver weight/total body weight) in phenobarbital-treated compared with normal rats. ANIT treatment in one rat was associated with a decrease of PCA° to 56%, resulting in an approximately 53% reduction in $R°_{Syn}$. Carbon tetrachloride treatment was the only pre-treatment studied which affected both PCA° and $k_d$ in a pro-hemorrhagic fashion (Table II). This resulted in an average of approximately 62% reduction in $R°_{Syn}$ in the carbon tetrachloride-treated animals. Overall, there was a highly significant positive relationship between PCA° and $R°_{Syn}$ (p<0.001).

Effects of Pretreatments on Vitamin K-Dependent Carboxylation:

In vitro characterization of rat hepatic vitamin K-dependent carboxylation in rats pretreated with ANIT, carbon tetrachloride, or phenobarbital revealed several differences from normal rats (Table III). Carbon tetrachloride pretreatment was associated with an approximately 20-30% reduction in $V/K_M$ in the two rats receiving 1.0 ml CCl$_4$/kg. These same two rats had a diminished amount of endogenous substrate, as measured by the normalized $P_\infty$. The ANIT and phenobarbital-pretreated rats had essentially normal values of $V/K_M$. However, phenobarbital-pretreated rats had a diminished amount of endogenous substrate when measured as a fraction of total microsomal protein, indicating a relative proliferation of non-vitamin K-dependent proteins in the microsomal fraction. On the other hand, the ANIT-treated rat had an approximately 50% increase in normalized $P_\infty$, indicating an increase in the amount of endogenous substrate when measured as a fraction of total microsomal protein. This increase may be the result of the generalized hypertrophy of hepatic smooth endoplasmic reticulum which follows ANIT administration (Lancet 2, 355-359; Lab. Invest. 28, 321-331).

Relationships Between in vitro and in vivo Activities:

The individual correlative relationships between each of two parameters ($V/K_M$ and normalized $P_\infty$) of in vitro vitamin K-dependent carboxylation and each of three parameters (PCA°, $k_d$, and $R°_{Syn}$) of in vivo vitamin K-dependent hemostatic function were quantified by calculating a non-parametric measure of concordance (i.e., Kendall's $\tau_b$) and a conventional measure of linear correlation (i.e., Pearson's product moment correlation coefficint, r). The results of these calculations are summarized in Table IV.

TABLE IV

Correlative relationships between vitamin K-dependent in vitro carboxylation and in vivo hemostatic function

| Parameters of in vivo Vitamin K-dependent Hemostatic Function | Parameters of In vitro vitamin K-dependent carboxylation | | | |
|---|---|---|---|---|
| | $V/K_M$ | | Normalized $P_\infty$ | |
| | r | $\tau_b$ | r | $\tau_b$ |
| PCA° | 0.715* | 0.500+ | 0.238 | 0.214 |
| $K_d$ | −0.440 | 0.000 | −0.257 | −0.429 |
| $R°_{Syn}$ | 0.787* | 0.643* | 0.073 | 0.500+ |

Probabilities for the tests of the null hypothesis that r = 0 or $\tau_b$ = 0 for n = 8:
*0.01 < p ≤ 0.05
+0.05 < p ≤ 0.10

Figure 7:
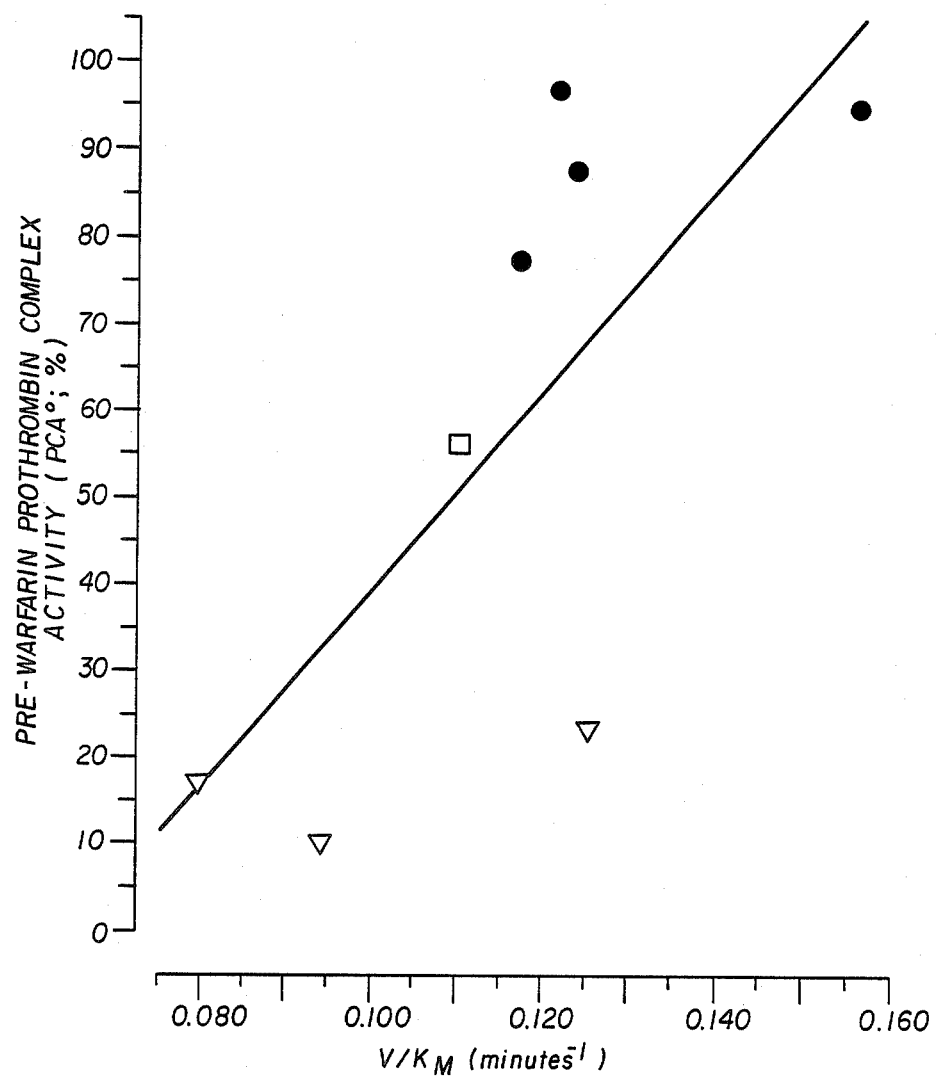
FIG. 7. Relationship between in vivo prewarfarin prothrombin complex activity (PCA°) and the in vitro intrinsic formation rate of carboxylated vitamin K-dependent proteins (V/$K_M$). Parameters shown were observed in normal (●), ANIT-treated (□), and $CCl_4$-treated (∇) rats. The linear least-squares regression line is superimposed (r=0.715 [0.01<p<0.05]; $\tau_b$=0.500).

Each of the in vivo parameters PCA° and $R°_{Syn}$ were significantly correlated with $V/K_M$, i.e., there is a positive relationship between the in vitro hepatic intrinsic formation rate of carboxylated vitamin K-dependent proteins and in vivo steady-state levels of PCA and the rate of synthesis of PCA (FIGS. 7 and 8). The correlation between $R°_{Syn}$ and $V/K_M$ is particularly impressive when viewed from the perspective of concordance, rather than linear correlation, since seven of the eight animals have mutually concordant data points. No parameter of in vivo vitamin K-dependent hemostatic function exhibited a significant correlation with the normalized $P_B$ paraxeter of in vitro vitamin K-dependent carboxylation, suggesting that the rate of carboxylation, rather than substrate availability, is the primary determinant of in vivo levels and rate of formation of PCA.

Rats pretreated with phenobarbital for 5 days were excluded from these analyses of in vivo-in vitro correlations since these rats exhibited a clear in vivo-in vitro discordance compared with the rats in the normal, ANIT, and carbon tetrachloride groups. Specifically, phenobarbital-treated rats had a marked increase in both $R°_{Syn}$ (average of 44% increase above normal rats) and $PCA°$ (average of 38% increase above normal rats), but the in vitro intrinsic formation rate for the livers harvested from these same rats showed essentially no difference from normal rats while there was a relative proliferation of non-vitamin K-dependent proteins in the microsomal fraction (Table III)

The above experiments have shown that the in vitro vitamin K-dependent carboxylation of precursors of vitamin K-dependent coagulation factors follows first-order kinetics, is inhibited by different vitamin K antagonists according to classical sigmoidal concentration-response relationships, and is correlated with in vivo turnover parameters of vitamin K-dependent coagulation factors. An in vitro detergent-free rat hepatic microsomal system was used to determine the time course of carboxylation of the endogenous microsomal substrates. Use of the native substrate avoided the potential problem of competition between native substrate and synthetic, exogenously added substrate, as well as the possibility of dissimilar kinetic properties due to the greater conformational-dependence of carboxylation of the native substrate protein compared with the pentapeptide substrate. Such differences in conformational dependence have been well illustrated for the case of a synthetic substrate for thrombin (Haemostasis 7, 109-112) The present assay system allowed the investigation of each vitamin K antagonist using the individual animal as his own control such that interanimal differences in responsiveness are accounted for. Furthermore, this assay system with its endogenous precursor substrate enabled investigations of relationships between specific in vitro and in vivo parameters of vitamin K-dependent coagulation factors.

The in vitro experimental system responds in a sigmoidal concentration response manner to six different vitamin K-antagonists, which represented different groups of chemicals. The order of potency of these vitamin K antagonists (from most potent to least potent) was TCP, phenindione, 2,6-DIP, chloro-$K_3$, chloro-$K_1$, and warfarin (FIG. 4), with average $IC_{50}$'s ranging from 1.23 M for TCP to 6.63 mM for warfarin (Table I). The observed $IC_{50}$ for warfarin is in good agreement with data obtained in an in vitro system measuring the inhibition of prothrombin procoagulant activity (Biochem. Biophys Res. Commun. 72, 619-625). In addition to the wide variability in sensitivity to different antagonists, the vitamin K-dependent carboxylation system also exhibited a significant interanimal variability in sensitivity to a given inhibitor (Table I). The frequency distribution of values of K and $P_\infty$ in the rat has been investigated separately in an effort to gain insight into the nature of this interanimal variability (Pharmacology of Rat Heptatic Vitamin K-Dependent Carboxylation, Doctoral Disseration, Duke University).

The mechanism of anticoagulant action of the vitamin K antagonists has not been unambiguously determined (CRC Crit. Rev. Biochem. 8, 191-223; Drugs and Nutrients. The Interactive Effects, 429-473). The different enzymes involved in vitamin K-dependent carboxylation, i.e., dithiothreitol-sensitive vitamin K reductase, DT-diaphorase, vitamin K epoxidase, and vitamin K 2,3-epoxide reductase can apparently all be pharmacologically inhibited. Recent studies have suggested that the anticoagulant action of warfarin is probably due to inhibition of both a dithiothreitol-sensitive vitamin K reductase, and vitamin K 2,3-epoxide reductase (J. Biol. Chem. 257, 4894-4901 and 257, 11210-11212). Deviation of the percent inhibition versus concentration plots for warfarin from a purely sigmoidal function (FIG. 3) can possibly be accounted for by either a difference in the potency of the two enantiomers of warfarin or by two different sites of action with different percent inhibition versus concentration relationships. The latter mechanism is compatible with recent in vitro findings that both isomers are equipotent inhibitors of vitamin K reductase and vitamin K 2, 3-epoxide reductase (J. Biol. Chem. 257, 4894-4901), although this proposed mechanism does not explain the differnce in in vivo potencies of the two warfarin isomers (J. Biol. Chem. 257, 4894-4901; J. Pharm. Pharmac. 24, 661-662). Thus, the mechanism of action of warfarin may also involve other pharmacological inhibitions.

The results presented for phenindione and chloro-$K_1$ indicate a substantially different slope for the percent inhibition-concentration plot compared with the other four antagonists. This difference in slope suggests that these two compounds differ in some apect of their mechanism of action from the other four antagonists (Drug Design, Vol. 1, 1-270), e.g., by inhibiting different enzymes involved in vitamin K-dependent carboxylation or by acting at different sites on the same enzyme. While in vitro studies had suggested that phenindione and warfarin share a common mechanism of action, namely, inhibition of vitamin $K_1$, 2,3-epoxide reductase (Biochem. Biophys. Res. Commun. 72, 619-625; Molecular Pharmacology 10, 373-380; Thromb. Diath. Haemorrh. 19, 611), studies in vivo showed a complete block of prothrombin synthesis after phenindione in the presence of only limited inhibition of vitamin K epoxide reductase (J. Pharmacol. Exp. Ther. 157, 672-680), suggesting the existence of an alternative mechanism of action of phenindione. Such an alternative mechanism of action, similar to that of chloro-$K_1$, can be postulated on the basis of a modified hypothesis of vitamin K action first proposed by Lowenthal et al. (Thromb. Diath. Haemorrh. 19, 611; J. Pharmacol. Exp. Ther. 143, 273-277; Science 164, 81-183), and supported by biochemical studies of Whitlon et al. (Biochemistry 17, 1371-1377) and Fasco et al. (J. Biol. Chem. 257, 4894-4901 and 257, 11210-11212). Vitamin K can be activated to its hydroquinone form, which binds reversibly to and is an essential cofactor for vitamin K-dependent carboxylase, via two alternative routes. The first route consists of the dithiothreitol-dependent vitamin K reductase, which is operative at relatively low vitamin K concentrations (has a low $K_M$) and is susceptible to irreversible inhibition by 3-substituted 4-hydroxycoumarins, while the second route consists of the NADH-dependent DT diaphorase (Biochem. J. 169, 95-101 and 194, 983-988), which is operative at relatively high vitamin K concentrations (has a high $K_M$) and has markedly lower sensitivity to inhibition by warfarin (Biochem. Biophys. Res. Commun. 104, 87-192). Chloro-$K_1$, however, has been found to act as a competitive inhibitor of vitamin K-dependent clotting factor synthesis while having essentially no effect on the warfarin-inhibitable mechanism (J. Pharmacol. Exp. Ther. 143, 273–277), suggesting that it was acting at the level of the vitamin K-dependent carboxylase. Thus, it is reasonable to postulate that chloro-$K_1$ and phenindione are competitive antagonists at the level of the vitamin K-dependent carboxylase, while TCP, 2,6-DIP, chloro-$K_3$, and warfarin exert their primary effect by diminishing the pool of vitamin $K_1$ hydroquinone, by one or more possible mechanisms.

Evidence was presented above for an in vitro-in-vivo correlation of parameters of vitamin K-dependent function. Specifically, the in vivo rate of synthesis of prothrombin complex activity was concordant with the in vitro intrinsic formation rate of carboxylated rat hepatic vitamin K-dependent proteins. In addition, a lesser concordant correlation was observed between the circulating plasma prothrombin complex activity and the in vitro intrinsic formation rate of carboxylated rat hepatic vitamin K-dependent proteins. These findings provide the first evidence that a more rapid rate of vitamin K-dependent carboxylation is indeed associated with a relatively large in vivo rat or synthesis of activity of the vitamin K-dependent prothrombin complex and a relatively hypercoagulable baseline state. Establishment of this in vivo-in vitro correlation provides further support for the utility of the present in vitro system due to its ability to determine the first-order rate constant of the vitamin K-dependent carboxylation of the endogenous substrate. In contrast, the amount of available hepatic precursors of vitamin K-dependent coagulation factors did not correlate with any parameter of in vivo rate of synthesis of prothrombin complex activity. This suggests that at least during hepatic injury, the rate of vitamin K-dependent carboxylation, rather than substrate availability, is the primary determinant of in vivo levels and rate of formation of prothrombin complex activity. It is of interest that the so-called coagulopoietins (Brit. J. Haematol. 24, 553–562; Annals N.Y. Acad. Sci. 370, 281–290), which are thought to be involved in a positive feedtack regulation for activity of circulating vitamin K-dependent coagulation factors, apparently also act by enhancing vitamin K-dependent carboxylation (Thromb. Res. 19, 111–118). This further suggests that the rate of carboxylation is intimately involved in the overall regulation of levels and activity of vitamin K-dependent coagulation factors Ihe invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A food composition for poisoning a rodent, which comprises a rodent foodstuff and as an active rodenticidal agent, an acute-poison or chronic-poison amount of a compound having the formula:

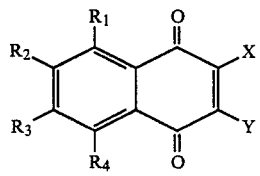

wherein X is Cl, Br, F, or I; Y is H, Cl, Br, F or I; and $R_1$–$R_4$ are each independently H, Cl, Br. F, I, $C_1$–$C_6$ alkyl, $C_1$–$C_6$ alkoxy, or $C_1$–$C_6$ alkoxyalkyl.

2. A food composition for poisoning a rodent, which ccmprises a rodent foodstuff which contains as an active rodenticidal agent, an acute-poison or chronic-poison amount of a compound having the formula:

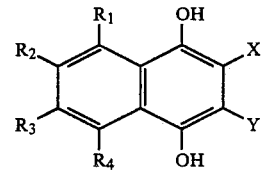

wherein X is Cl, Br, F, or I; Y is H, Cl, Br, F, or I; and $R_1$–$R_4$ are each independently H, Cl, Br, F, I, $C_1$–$C_6$ alkyl, $C_1$–$C_6$ alkoxy, or $C_1$–$C_6$ alkoxyalkyl.

3. The composition of claim 1, wherein $R_1$–$R_4$ and Y in said compound are each H.

4. The composition of claim 2, wherein $R_1$–$R_4$ and Y in said compound are each H.

5. A food composition according to claim 1, wherein said compound is 2-chloro-1,4-naphthoquinone.

6. A food composition according to claim 2, wherein said compound is 2-chloro-1,4-naphthohydroquinone.

7. A food composition according to claim 1, wherein said rodenticidal compound is contained in said food composition in an amount of 0.00001 to 0.1% by wt.

8. A food composition according to claim 2, wherein said rodenticidal compound is contained in said food composition in an amount of 0.005 to 0.05% by wt.

9. A method for poisoning a rodent, which comprises providing to said rodent for consumption, a food composition comprising an acute-poison or chronic-poison amount of a compound having the formula:

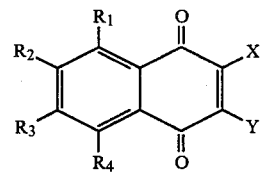

wherein X is Cl, Br, F, or I; Y is H, Cl, Br, F, or I; and $R_1$–$R_4$ are each independently H, Cl, Br, F, I, $C_1$–$C_6$ alkyl, $C_1$–$C_6$ alkoxyl, or $C_1$–$C_6$ alkoxyalkyl.

10. A method for poisoning a rodent, which comprises providing to said rodent for consumption, a food composition comprising an acute poison or chronic poison amount of a compound having the formula:

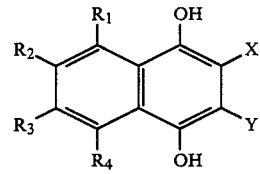

wherein X is Cl, Br, F, or I; Y is H, Cl, Br, F, or I; and $R_1$–$R_4$ are each independently H, Cl, Dr, F, I, $C_1$–$C_6$ alkyl, $C_1$–$C_6$ alkoxyl, or $C_1$–$C_6$ alkoxyalkyl.

11. A method according to claim 9, wherein said rodent is a rat or a mouse.

12. A method according to claim 10, wherein said rodent is a rat or a mouse.

13. A method according to claim 9, wherein said compound is 2-chloro-1,4-naphthoquinone.

14. A method according to claim 10, wherein said compound is 2-chloro-1,4-naphthohydroquinone.

15. A method according to claim 9, wherein said food composition comprises a rodent foodstuff or bait which is impregnated with said compound.

16. A method according to claim 10, wherein said food composition comprises a rodent foodstuff or bait which is impregnated with said compound.

17. A method according to claim 9, wherein said foodstuff or bait contains from 0.00001 to 0.01% by wt. of said compound.

18. A method according to claim 10, wherein said foodstuff or bait contains from 0.005 to 0.05% by wt. of said compound.

* * * * *

UNITED STATES PATENT AND TRADEMARK OFFICE
CERTIFICATE OF CORRECTION

PATENT NO. : 4,734,282

DATED : MARCH 29, 1988

INVENTOR(S) : THORIR D. BJORNSSON ET AL

Page 1 of 3

It is certified that error appears in the above-identified patent and that said Letters Patent is hereby corrected as shown below:

In Field [56], under "OTHER PUBLICATIONS", line 3, after "Association," insert --1953,--;

line 8, delete "Medical Association" and insert --Chemical Society--.

Column 1, line 29, delete "Vitamin" and insert --vitamin--;

line 36, delete "Vitamin" and insert --vitamin--;

line 37, delete "Vitamin" and insert --vitamin--;

line 43, delete "anti-coagulants" and insert --anticoagulants--;

line 61, change "hydroxy coumarin" to --hydroxycoumarin--.

Column 2, line 26, delete "Vitamin" and insert --vitamin--.

Column 4, line 35, delete "tetra-chloride-pre" and insert --tetrachloride-pre--.

Column 5, line 52, delete "chronicpoison" and insert --chronic-poison--;

line 62, after "0.05", delete "to".

UNITED STATES PATENT AND TRADEMARK OFFICE
CERTIFICATE OF CORRECTION

PATENT NO. : 4,734,282
DATED : MARCH 29, 1988
INVENTOR(S) : THORIR D. BJORNSSON ET AL

It is certified that error appears in the above-identified patent and that said Letters Patent is hereby corrected as shown below:

Column 6, line 4, insert "as" after "such";

line 44, delete "1970" and insert --(1970)--.

Column 7, line 36, delete "3-phytyl-1, 4-naphthoquinone)" and insert --3-phytyl-1,4-naphthoquinone)--;

line 60, delete "detergentfree" and insert --detergent free--;

line 61, delete "detergentsolubilized" and insert --detergent solubilized--.

Column 10, line 20, delete "27°: and insert --27°C--;

line 64, delete "$\ln(P_\infty[P_\infty-P])$" and insert --$\ln(P_\infty/[P_\infty-P])$--.

Column 11, line 33, delete "$(V/K_M)$" and insert --$(V/K_M)$ in--.

Column 12, line 68, delete "Rate" and insert --rat--.

Column 13, line 49, delete "a typical" and insert --atypical--.

Column 14, line 27, delete "(0.001<p 0.01)" and insert --(0.001<p<0.01)--.

UNITED STATES PATENT AND TRADEMARK OFFICE
CERTIFICATE OF CORRECTION

PATENT NO. : 4,734,282

DATED : MARCH 29, 1988

INVENTOR(S) : THORIR D. BJORNSSON ET AL

It is certified that error appears in the above-identified patent and that said Letters Patent is hereby corrected as shown below:

Column 14, line 59 (Table II), delete "$OCl_4$", and insert --$CCl_4$--.

Column 16, line 66, delete "$P_B$ paraxeter" and insert --$P_\infty$ parameter--.

Column 18, line 28, delete "apect" and insert --aspect--.

Column 19, line 46, delete "Ihe" and insert --The--.

Signed and Sealed this

Fourteenth Day of February, 1989

Attest:

DONALD J. QUIGG

Attesting Officer

Commissioner of Patents and Trademarks